(12) United States Patent
Giger et al.

(10) Patent No.: US 7,123,762 B2
(45) Date of Patent: Oct. 17, 2006

(54) METHOD AND SYSTEM FOR RISK-MODULATED DIAGNOSIS OF DISEASE

(75) Inventors: Maryellen L. Giger, Elmhurst, IL (US); Zhimin Huo, Chicago, IL (US); Carl J. Vyborny, Riverside, IL (US)

(73) Assignee: University of Chicago, Chicago, IL (US)

( * ) Notice: Subject to any disclaimer, the term of this patent is extended or adjusted under 35 U.S.C. 154(b) by 769 days.

(21) Appl. No.: 10/360,814

(22) Filed: Feb. 10, 2003

(65) Prior Publication Data

US 2003/0174873 A1 Sep. 18, 2003

Related U.S. Application Data

(60) Provisional application No. 60/354,523, filed on Feb. 8, 2002.

(51) Int. Cl.
*G06K 9/00* (2006.01)
*A61B 5/00* (2006.01)

(52) U.S. Cl. ...................................... 382/132; 600/408

(58) Field of Classification Search ................ 382/128, 382/132; 128/922; 600/408; 378/37
See application file for complete search history.

(56) References Cited

U.S. PATENT DOCUMENTS 6,112,112 A 8/2000 Gilhuijs et al. ............. 600/425

6,282,305 B1 * 8/2001 Huo et al. ................... 382/128
6,484,144 B1 11/2002 Martin et al. .................. 705/2
2001/0031076 A1 * 10/2001 Campanini et al. ......... 382/128

OTHER PUBLICATIONS

Tahoces et al., "Computer-assisted diagnosis: the classification of mammographic breast parenchymal patterns," Phys. Med. Biol. 40 (1995) 103-117.*
Huo et al., "Computerized analysis of mammographic parenchymal patterns for breast cancer risk assessment: Feature selection," Med. Phys. 27 (1) Jan. 4-12, 2000.*

* cited by examiner

*Primary Examiner*—Andrew W. Johns
(74) *Attorney, Agent, or Firm*—Oblon, Spivak, McClelland, Maier & Neustadt, P.C.

(57) ABSTRACT

A method of calculating a disease assessment by analyzing a medical image, comprising (1) extracting at least one lesion feature value from the medical image; (2) extracting at least one risk feature value from the medical image; and (3) determining the disease assessment based on the at least one lesion feature value and the at least one risk feature value. The method employs lesion characterization for characterizing the lesion, and risk assessment based on the lesion's surroundings, i.e., the environment local and distal to the lesion. Computerized methods both characterize mammographic lesions and assess the breast parenchymal pattern on mammograms, resulting in improved characterization of lesions for specific subpopulations, combining the benefits of both techniques.

22 Claims, 8 Drawing Sheets

METHOD AND SYSTEM FOR RISK-MODULATED DIAGNOSIS OF DISEASE

CROSS-REFERENCE TO RELATED APPLICATION

The present application claims priority to U.S. Provisional Application No. 60/354,523, the contents of which are incorporated herein by reference.

STATEMENT REGARDING FEDERALLY SPONSORED RESEARCH

The present invention was made in part with U.S. Government support under NIH Grants CA79711 and CA89452. The U.S. Government may have certain rights to this invention.

BACKGROUND OF THE INVENTION

Field of the Invention

The invention relates generally to the field of computer-aided diagnosis in the detection, characterization, diagnosis, and/or assessment of normal and diseased states.

The present invention also generally relates to computerized techniques for automated analysis of digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 5,732,697; 5,740,268; 5,790,690; 5,832,103; 5,873,824; 5,881,124; 5,931,780; 5,974,165; 5,982,915; 5,984,870; 5,987,345; 6,011,862; 6,058,322; 6,067,373; 6,075,878; 6,078,680; 6,088,473; 6,112,112; 6,138,045; 6,141,437; 6,185,320; 6,205,348; 6,240,201; 6,282,305; 6,282,307; 6,317,617; as well as U.S. patent applications Ser. Nos. 08/173,935; 08/398,307 (PCT Publication WO 96/27846); 08/536,149; Ser. Nos. 08/900,189; 09/027,468; 09/141,535; 09/471,088; 09/692,218; 09/716,335; 09/759,333; 09/760,854; 09/773,636; 09/816,217; 09/830,562; 09/818,831; 09/842,860; 09/860,574; 60/160,790; 60/176,304; 60/329,322; 09/990,311; 09/990,310; 60/332,005; and 60/331,995; as well as co-pending U.S. patent applications Ser. Nos. 60/332,005, 60/180,162, and 60/207,401; as well as PCT patent applications PCT/US98/15165; PCT/US98/24933; PCT/US99/03287; PCT/US00/41299; PCT/US01/00680; PCT/US01/01478 and PCT/US01/01479, all of which are incorporated herein by reference.

The present invention includes use of various technologies referenced and described in the above-noted U.S. Patents and Applications, as well as described in the non-patent references identified in the following LIST OF REFERENCES by the author(s) and year of publication and cross-referenced throughout the specification by reference to the respective number, in parentheses, of the reference:

LIST OF REFERENCES

1. Feig S A: Decreased breast cancer mortality through mammographic screening: Results of clinical trials. Radiology 167:659–665, 1988.
2. Tabar L, Fagerberg G, Duffy S W, Day N E, Gad A, Grontoft O: Update of the Swedish two-county program of mammographic screening for breast cancer. Radiol Clin North Am 30:187–210, 1992.
3. Smart C R, Hendrick R E, Rutledge J H, Smith R A: Benefit of mammography screening in women ages 40 to 49 years: Current evidence from randomized controlled trials. Cancer 75:1619–26, 1995.
4. Bassett L W, Gold R H: Breast Cancer Detection: Mammography and Other Methods in Breast Imaging New York: Grune and Stratton, 1987.
5. Kopans D B: Breast Imaging. Philadelphia: J B Lippincott, 1989.
6. Brown M L, Houn F, Sickles E A, Kessler L G: Screening mammography in community practice: positive predictive value of abnormal findings and yield of follow-up diagnostic procedures. AJR 165:1373–1377, 1995.
7. Giger M L: Computer-aided diagnosis. In: Syllabus: A Categorical Course on the Technical Aspects of Breast Imaging, edited by Haus A, Yaffe M. Oak Brook, Ill.: RSNA Publications, 1993, pp. 272–298.
8. Vyborny C J, Giger M L: Computer vision and artificial intelligence in mammography. AJR 162:699–708, 1994.
9. Giger M L, Huo Z, Kupinski M A, Vyborny C J: "Computer-aided diagnosis in mammography", In: Handbook of Medical Imaging, Volume 2. Medical Imaging Processing and Analysis, (Sonka M, Fitzpatrick M J, eds) SPIE, pp. 915–1004, 2000.
10. D'Orsi C J, Bassett L W, Feig S A, Jackson V P, Kopans D B, Linver M N, Sickles E A, Stelling C B: Breast Imaging Reporting and Data System (BI-RADS). Reston, Va. (American College of Radiology), 1998.
11. Getty D J, Pickett R M, D'Orsi C J, Swets J A: Enhanced interpretation of diagnostic images. Invest. Radiol. 23: 240–252, 1988.
12. Swets J A, Getty D J, Pickett R M, D'Orsi C J, Seltzer S E, McNeil B J: Enhancing and evaluating diagnostic accuracy. Med Decis Making 11:9–18, 1991.
13. Cook H M, Fox M D: Application of expert systems to mammographic image analysis. American Journal of Physiologic Imaging 4: 16–22, 1989.
14. Gale A G, Roebuck E J, Riley P, Worthington B S, et al.: Computer aids to mammographic diagnosis. British Journal of Radiology 60: 887–891, 1987.
15. Getty D J, Pickett R M, D'Orsi C J, Swets J A: Enhanced interpretation of diagnostic images. Invest. Radiol. 23: 240–252, 1988.
16. Swett H A, Miller P A: ICON: A computer-based approach to differential diagnosis in radiology. Radiology 163: 555–558, 1987.
17. Huo Z, Giger M L, Vyborny C J, Bick U, Lu P, Wolverton D E, Schmidt R A: Analysis of spiculation in the computerized classification of mammographic masses" Medical Physics 22:1569–1579, 1995.
18. Jiang Y, Nishikawa R M, Wolverton D E, Giger M L, Doi K, Schmidt R A, Vyborny C J: Automated feature analysis and classification of malignant and benign clustered microcalcifications. Radiology 198(3):671–678, 1996.
19. Ackerman L V, Gose E E: Breast lesion classification by computer and xeroradiography. Breast Cancer 30:1025–1035, 1972.
20. Patrick E A, Moskowitz M, Mansukhani V T, Gruenstein E I: Expert learning system network for diagnosis of breast calcifications. Invest Radiol 16: 534–539, 1991.
21. Huo Z, Giger M L, Vyborny C J, Wolverton D E, Schmidt R A, Doi K: Automated computerized classification of malignant and benign mass lesions on digitized mammograms. Academic Radiology 5: 155–168, 1998.

22. Jiang Y, Nishikawa R M, Schmidt R A, Metz C E, Giger M L, Doi K: Improving breast cancer diagnosis with computer-aided diagnosis. Academic Radiology 6: 22–33, 1999.
23. Huo Z, Giger M L, Metz C E: Effect of dominant features on neural network performance in the classification of mammographic lesions. PMB 44: 2579–2595, 1999.
24. Huo Z, Giger M L, Vyborny C J, Wolverton D E, Metz C E: Computerized classification of benign and malignant masses on digitized mammograms: a robustness study. Academic Radiology 7:1077–1084 2000.
25. American Cancer Society. Cancer facts and Figures-1998. New York, N.Y. 1998; p. 20.
26. King M-C. Breast cancer genes: how many, where, and who are they? Nature Genet 1992; 2:250–290.
27. Offit K and Brown K. Quantitation of familial cancer risk: a resource for clinical oncologists. J Clin Oncol 1994; 86:620–625.
28. King M-C, Rowell S and Love S M. Inherited breast and ovarian cancer. JAMA 1993; 269:1975–1980.
29. King M-C. Breast cancer genes: how many, where, and who are they? Nature Genet 1992; 2:250–290.
30. Hall J M, Lee M K and Morrow J. Linkage of early-onset familial breast cancer to chromosome 17q21. Science 1990; 250:1684–1689.
31. Malkin D, Li F P and Strong L C. Germ line p53 mutations in a familial syndrome of breast cancer, sarcomas, and other neoplasms. Science 1990; 250:1233–1238.
32. Offit K. Clinical Cancer Genetics: Risk Counseling and Management. New York, Wiley-Liss, 1998.
33. Struewing J P, Hartge P, Wacholder S, Baker S M, Berlin M, McAdams M, Timmerman M M, Brody L C and Tucher M A. The risk of cancer associated with specific mutations of BRCA1 and BRCA2 among ashkenazi jews. N Engl J Med 1997; 336:1401–1408.
34. Easton D F, Ford D and Bishop T D. Breast and ovarian cancer incidence in BRCA1-mutation carriers. Am J Hum Genet 1995; 56:256–271.
35. Newman B, Austin M A, Lee M and King M-C. Inheritance of human breast cancer: evidence for autosomal dominant transmission in high risk families. Proc Natl Acad Sci USA 1988; 85:3044–3048.
36. Claus E B, Risch N and Thompson W D. Genetic analysis of breast cancer in the cancer and steroid hormone study. Am J Hum Genet 1991; 48:232–242.
37. Clark-Paul K C, Thomas R S and Ketcham A S. Estrogen and the breast. Surg Oncol Clin North 1993; 2:135–144.
38. Miller B A. The epidemiology of breast cancer. In Ames F C, Blumenschein G R and Montague E D (eds): Current Controversies in Breast Cancer. Austin, Tex. The University of Texas Press, 1984;
39. Gail M H and Benichou J. Assessing the risk of breast cancer in individuals. In DeVita V T, Hellman S and Rosenberg S A (eds): Cancer Prevention. Philadelphia. J. B. Lippincott, 1992; 1–15.
40. Kosary C L, Ries L A G, Miller B A, Harris A and Edwards B K. SEER cancer statistics review, 1973–1992: tables and graphs. Bethesda, Md., National Cancer Institute, 1995
41. Boyd N F, Byng J and Jong R. Quantitative classification of mammographic densities and breast cancer risk: results from the Canadian National Breast Screening Study. J Natl Cancer Inst 1995; 87:670–675.
42. Boyd N F, O'Sullivan B, Campbell J E, Fishell E, Simor I and Cooke G. Mammographic signs as risk factors for breast cancer. Br J Cancer 1982; 45:185–193.
43. Wolfe J N, Saftlas A F and Salane M. Mammographic parenchymal patterns and quantitative evaluation of mammographic densities: a case-control study. Am J Roentgenol 1987; 148:1087–1092.
44. Brisson J, Morrison A S and Khalid N. Mammographic parenchymal features and breast cancer in the Breast Cancer Detection Demonstration Project. J Natl Cancer Inst 1980; 80:1534–1540.
45. Saftlas A F, Hoover R N, Brinton L A, Szklo M, Olson D R, Salane M and Wolfe J N. Mammographic densities and risk of breast cancer. Cancer 1991; 67:2833–2838.
46. Byrne C, Schairer C, Wolfe J, Parekh N, Salane M, Brinton L A, Hoover R and Haile R. Mammographic features and breast cancer risk: effects with time, age, and menopause status. J Natl Cancer Inst 1995; 87:1622–1629.
47. Claus E B, Risch N and Thompson W D. Autosomal dominant inheritance of early-onset breast cancer: Implications for risk prediction. Cancer 1993; 73:643–651.
48. Gail M H, Brinton L A, Byar D P, Corle D K, Green S B, Schairer C and Mulvihill J J. Projecting individualized probabilities of developing breast cancer of white females who are being examined annually. J Natl Cancer Inst 1989; 81:1879–1886.
49. Bondy M L, Lustbader E D, Halabi S, Ross E and Vogel V G. Validation of a breast cancer risk assessment model in women with a positive family history. L Natl Cancer Inst 1994; 86:620–625.
50. Spiegelman D, Colditz G A, Hunter D and Hertzmark E. Validation of the Gail et al. model for predicting individual breast cancer risk. J Natl Cancer Inst 1989; 86:600–607.
51. Hoskins K F, Stopfer J E and Calzone K A. Assessment and counseling for women with a family history of breast cancer. JAMA 1995; 273:577–586.
52. Gail M H and Benichou J. Epidemiology and biostatistics program of the national cancer institute. J Natl Cancer Inst 1994; 86:573–575.
53. Wolfe J. Breast patterns as an index of risk for developing breast cancer. Am J Roentgenol 1976; 126:1130–1139.
54. Warner E, Lockwood G, Math M, Tritchler D and Boyd N F. The risk of breast cancer associated with mammographic parenchymal patterns: a meta-analysis of the published literature to examine the effect of method of classification. Cancer Detection and Prevention 1992; 16:67–72.
55. Egan R L and Mosteller R C. Breast cancer mammography patterns. Cancer 1997; 40:2087–2090.
56. Boyd N F, O'Sullivan B and Fishell E. Mammographic patterns and breast cancer risk: methodological standards and contradictory results. J Natl Cancer Inst 1984; 72:1253–1259.
57. Oza A M and Boyd N F. Mammographic parenchymal patterns: a marker of breast cancer risk. Epidemiologic Rev 1993; 15:196–208.
58. Ma L, Fishell E and Wright B. Case-control study of factors associated with failure to detect breast cancer by mammography. J Natl Cancer Inst 1992; 84:781–785.
59. Whitehead J, Calile T and Kopecky K J. Wolfe mammographic parenchymal patterns: a study of the masking hypothesis of Egan and Mosteller. Cancer 1985; 56:1280–1286.
60. Boyd N F, O'Sullivan B O, Fishell E, Simor I and Cooke G. Mammographic patterns and breast cancer risk: methodological standards and contradictory results. J Natl Cancer Ints 1984; 72:1253–1259.

61. Magnin I E, Cluzeau F and Odet C L. Mammographic texture analysis: an evaluation of risk for developing breast cancer. Optical Engineering 1986; 25:780–784.
62. Caldwell C B, Stapleton S J, Holdsworth D W, Jong R A, Weiser W J, Cooke C and Yaffe M J. Characterization of mammographic parenchymal pattern by fractal dimension. Phys Med Biol 1990; 35:235–247.
63. Taylor P, Hajnal S, Dilhuydy M -H and Barreau B. Measuring image texture to separate "difficult" from "easy" mammograms. British J Rad 1994; 67:456–463.
64. Tahoces P, Correa J, Souto M, Gomes L and Vidal J. Computer-assisted diagnosis: The classification of mammographic breast parenchymal patterns. Phys Med Biol 1995; 40:103–117.
65. Byng J W, Yaffe M J, Lockwood G A, Little L E, Tritchler D L and Boyed N F. Automated analysis of mammographic densities and breast carcinoma risk. Cancer 1997; 88:66–74.
66. Byng J, Boyd N, Fishell E, Jong R and Yaffe M. Automated analysis of mammographic densities. Phys Med Biol 1996; 1996:909–923.
67. Metz C E. ROC methodology in radiologic imaging. Invest Radiol 1986; 21:720–733.
68. Huo Z, Giger M L, Wolverton D E, Zhong W, Cumming S, Olopade O I: Computerized analysis of mammographic parenchymal patterns for breast cancer risk assessment: Feature selection. Medical Physics 27: 4–12, 2000.
69. Bick U, Giger M L, et al: A new single-image method for computer-aided detection of small mammographic masses. Proc. CAR '95, Lemke H U, Inamura K, Jaffe C C, Vannier M W, eds. pgs. 357–363, 1995.
70. Amadasum M and King R. Texture features corresponding to texture properties. IEEE Trans on System, Man and Cybernetics 1989; 19:1264–1274.
71. Jain A K. Fundamentals of Digital Image Processing. Englewood Cliffs, N.J., Prentice-Hall, 1986.
72. Katsuragawa S, Doi K, MacMahon H, Monnier-Cholley L, Ishida T and Kabayashi T. Classification of normal and abnormal lungs with interstitial disease by rule-based method and artificial neural networks. J Digit Imaging 1997; 10:108–114.
73. Caligiuri P, Giger M L, Favus M J, Jia H, Doi K and Dixon L B. Computerized radiographic analysis of osteoporosis: Preliminary evaluation. Radiology 1993; 186:471–474.

In addition, the following patents and patent applications may be considered relevant to the field of the present invention:

Doi K, Chan H-P, Giger M L: Automated systems for the detection of abnormal anatomic regions in a digital x-ray image. U.S. Pat. No. 4,907,156, March 1990.
Giger M L, Doi K, Metz C E, Yin F-F: Automated method and system for the detection and classification of abnormal lesions and parenchymal distortions in digital medical images. U.S. Pat. No. 5,133,020, July 1992.
Doi K, Matsumoto T, Giger M L, Kano A: Method and system for analysis of false positives produced by an automated scheme for the detection of lung nodules in digital chest radiographs. U.S. Pat. No. 5,289,374, February 1994.
Nishikawa R M, Giger M L, Doi K: Method for computer-aided detection of clustered microcalcifications from digital mammograms. U.S. Pat. No. 5,537,485, July 1996.
Giger M L, Doi K, Lu P, Huo Z: Automated method and system for improved computerized detection and classification of mass in mammograms. U.S. Pat. No. 5,832,103, November, 1998.
Giger M L, Bae K, Doi K: Automated method and system for the detection of lesions in medical computed tomographic scans. U.S. Pat. No. 5,881,124, March, 1999.
Bick U, Giger M L: Method and system for the detection of lesions in medical images. U.S. patent allowed.
Giger M L, Zhang M, Lu P: Method and system for the detection of lesions and parenchymal distortions in mammograms. U.S. Pat. No. 5,657,362, August, 1997.
Giger M L, Kupinski M A: Automatic analysis of lesions in medical images. U.S. Pat. No. 6,138,045, Oct. 24, 2000.
Huo Z, Giger M L: Method and system for the computerized assessment of breast cancer risk. U.S. Pat. No. 6,282,305, Aug. 28, 2001.
Giger M L, Al-Hallaq H, Wolverton D E, Bick U: Method and system for the automated analysis of lesions in ultrasound images. U.S. Pat. No. 5,984,870, Nov. 16, 1999.
Gilhuijs K, Giger M L, Bick U: Method and system for the automated analysis of lesions in magnetic resonance images. U.S. patent Ser. No. 08/900,188 allowed.
Gilhuijs K, Giger M L, Bick U: Method and system for the assessment of tumor extent. U.S. patent Ser. No. 09/156,413. allowed.
Armato S G, Giger M L, MacMahon H: Method, system and computer readable medium for the two-dimensional and three-dimensional detection of lesions in computed tomography scans. U.S. Pat. pending
Giger M L, Vybomy C J, Huo Z, Lan L: Method, system and computer readable medium for an intelligent search workstation for computer assisted interpretation of medical images. U.S. patent Ser. No. pending 09/773,636.
Drukker K, Giger M L, Horsch K, Vybomy C J: Automated method and system for the detection of abnormalities in sonographic images. U.S. patent Ser. No. pending 60/332,005.

The contents of each of the above references, including patents and patent applications, are incorporated herein by reference. The techniques disclosed in the patents, patent applications, and other references can be utilized as part of the present invention.

DISCUSSION OF THE BACKGROUND

The inventors' research, findings, and analysis are discussed in this Background section along with that of others; accordingly, discussion in this section does not constitute an admission that the discussed material constitutes "prior art."

Breast cancer remains a disease without a cure unless diagnosed at a sufficiently early stage, and subsequently surgically removed, irradiated, or eradicated with chemotherapy. Major research issues include those focused on genetic and molecular forms of detection and treatment, and those focused on anatomical levels of prevention, detection, and treatment. In these various areas, the role of the human interpreter (e.g., oncologist, radiologist, pathologist, surgeon, or primary care physician) varies. However, the very presence of a human interpreter introduces subjective judgment into the decision-making process—whether it be in the initial detection (or misdetection) of a lesion on a mammogram or in the surgical decision regarding appropriate incision. Thus, while ongoing research is needed in the biological aspects of cancer, in the physical aspects of instrumentation to better "see" the cancer, and in the biological/chemical/physical aspects of therapy, research is also needed for improving the role of the human in the overall management of the patient. Multi-modality and multi-disciplinary decision-making on patient management, requiring inputs from oncologists, pathologists, radiologists, surgeons, and risk clinic physicians, can be quite subjective, as is often evident during case management conferences. Although "subjective" does not necessarily mean "poor judgment," it does permit sub-optimal and inconsistent decision making.

Breast cancer is the leading cause of death for women in developed countries. Detection of breast cancer in an early stage increases treatment success dramatically, and hence screening for breast cancer of women over 40 years of age is generally recommended. Current methods for detecting and diagnosing breast cancer include mammography, sonography (also referred to as ultrasound), and magnetic resonance imaging (MRI).

Mammography is the most effective method for the early detection of breast cancer, and it has been shown that periodic screening of asymptomatic women does reduce mortality (Refs. 1–6). Many breast cancers are detected and referred for surgical biopsy on the basis of a radiographically detected mass lesion or cluster of microcalcifications. Although general rules for the differentiation between benign and malignant mammographically identified breast lesions exist, considerable misclassification of lesions occurs with the current methods. On average, less than 30% of masses referred for surgical breast biopsy are actually malignant.

Computerized analysis schemes are being developed to aid in distinguishing between malignant and benign lesions in order to improve both sensitivity (true positive rate) and specificity (true negative rate). Comprehensive summaries of investigations in the field of mammography CAD (computer-aided diagnosis) have been published by Giger and colleagues (Refs. 7–9). Investigators have used computers to aid in the decision-making process regarding likelihood of malignancy and patient management using human-extracted features and BI-RADS (Refs. 10–13). Such methods are dependent on the subjective identification and interpretation of the mammographic data by human observers. Gale et al. (Ref. 14) and Getty et al. (Ref. 15) both developed computer-based classifiers, which take as input, diagnostically-relevant features obtained from radiologists' readings of breast images. Getty et al. found that with the aid of the classifier, community radiologists performed as well as unaided expert mammographers in making benign-malignant decisions. Swett et al. (Ref. 16) developed an expert system to provide visual and cognitive feedback to the radiologist using a critiquing approach combined with an expert system. Other investigators have developed methods based on computer-extracted features (Refs. 17–24).

The benefit of using computer-extracted features is the objectivity and reproducibility of the result. Radiologists employ many radiographic image features, which they seem to extract and interpret simultaneously and instantaneously. Thus, the development of methods using computer-extracted features requires, besides the determination of which individual features are clinically significant, the computerized means for the extraction of each such feature. Spatial features, which are characteristic of lesions, have been shown to be extractable by a computer analysis of the mammograms and to be useful in distinguishing between malignant and benign. Most methods are evaluated in terms of their ability to distinguish between malignant and benign lesions, although a few have been evaluated in terms of patient management (i.e., return to screening vs. biopsy). It is important to state that while one of the aims of computerized classification is to increase sensitivity (true positive rate), another aim of computerized classification is to reduce the number of benign cases sent for biopsy. Such a reduction will be clinically acceptable only if it does not result in unbiopsied malignant cases, however, since the "cost" of a missed cancer is much greater than misclassification of a benign case. Thus, computer classification schemes should be developed to improve specificity (true negative rate) but not at the loss of sensitivity (true positive rate). It has been shown that the computerized analysis of mass lesions (Refs. 17, 21) and clustered microcalcifications (Refs. 18, 22) on digitized mammograms yields performances similar to an expert mammographer and significantly better than average radiologists in the task of distinguishing between malignant and benign lesions.

The potential usefulness of computer-aided diagnosis as an aid to radiologists in the characterization and classification of mass lesions in mammography is being investigated. Observer studies have shown that such a system can aid in increasing the diagnostic accuracy of radiologists both in terms of sensitivity (true positive rate) and specificity (true negative rate). The mass classification method includes three components: 1) automated segmentation of mass regions, 2) automated feature-extraction, and 3) automated classification. The method was initially trained with 95 mammograms containing masses from 65 patients. Features related to the margin, shape, and density of each mass were extracted automatically from the image data and merged into an estimate of the likelihood of malignancy (Refs. 17, 21, 23, 24). These features include a spiculation measure (FIG. 1), a margin definition feature (FIG. 2), and two density measures. The round-robin performance of the computer in distinguishing between benign and malignant masses was evaluated by receiver operating characteristic (ROC) analysis (Ref. 21). The computer classification scheme yielded an Az value of 0.94, similar to that of an experienced mammographer (Az=0.91) and statistically significantly higher than the average performance of five radiologists with less mammographic experience (Az=0.81) (FIG. 3). With the database used, the computer scheme achieved, at 100% sensitivity, a positive predictive value of 83%, which was 12% higher than that of the experienced mammographer, and 21% higher than that of the average performance of the less experienced mammographers at a p-value of less than 0.001 (Ref. 21).

The computerized mass classification method was independently evaluated on a 110-case database consisting of 50 malignant and 60 benign cases (Ref. 24). The effects of variations in (1) case mix and (2) the film digitization technique, on the performance of the method were assessed. Categorization of lesions as malignant or benign using the computer achieved an Az value (area under the receiver operating characteristic (ROC) curve) of 0.90 on the prior training database (Fuji scanner digitization) in a round-robin evaluation, and Az values of 0.82 and 0.81 on the independent database for Konica and Lumisys digitization formats, respectively. However, in the statistical comparison of these performances, a statistical significant difference between the performance on the training database and that on the independent validation database (p-values >0.10) was not shown. Thus, the computer-based method for the classification of lesions on mammograms was shown to be robust to variations in case mix and film digitization technique (Ref. 24).

The breast is composed primarily of two components, fibroglandular tissue and fatty tissue. The average breast consists of 50% fibroglandular tissue and 50% fat. Fibroglandular tissue is a mixture of fibrous connective tissue and the glandular epithelial cells that line the ducts of the breast (the parenchyma). The major breast diseases develop from the terminal ductal lobular units of the breast, and arise predominantly from the epithelial cells that line the ducts, although the fibrous or connective tissue can also be involved. It is thought by most experts that malignant breast disease develops through a process that starts with epithelial hyperplasia, i.e., an increase in the number of epithelial cells. Epithelial hyperplasia can progress to atypical hyperplasia in which the epithelial cells not only increase in number, but also change in a way that is not normal for these cells. The process, at this stage, is believed to be reversible. Once a certain criterion level of atypia is reached, the diagnosis of carcinoma-in-situ can be made, in which there is no invasion of malignant cells outside of the duct. The process of malignant transformation is considered irreversible at this stage. In the last phase of development, the cancer cells break out of the ductal walls and invade the surrounding stromal tissue, and at this point the disease is called infiltrating or invasive carcinoma. Most (80%–85%) breast carcinomas can be seen on a mammogram as a mass, a cluster of tiny calcifications, or a combination of both. Other mammographic abnormalities are of lesser specificity and prevalence than masses and/or calcifications, and include skin or nipple changes, abnormalities in the axilla, asymmetric density, and architectural distortion.

Clinical acquisition of x-ray mammograms is a rather complicated procedure and requires specific techniques in order to obtain high quality images. Attenuation differences between various structures within the breast contribute to image contrast. Due to the similar composition of breast structures and the physical manifestations of breast carcinoma, screen-film mammographic imaging must be substantially different from general radiographic imaging. Low-energy x-rays are required to enhance the ability to differentiate between normal tissues and carcinoma. The radiological appearance of the breast varies between individuals because of variations in the relative amounts of fatty and fibroglandular tissue. Since fat has a lower effective atomic number than that of fibroglandular tissue, there is less x-ray attenuation in fatty tissue than in fibroglandular tissue. Fat appears dark (i.e., higher optical density) on a mammogram, while fibroglandular tissue appears light (i.e., lower optical density) on a mammogram. Regions of brightness associated with fibroglandular tissue are normally referred to as "mammographic density."

Breast cancer risk assessment provides an opportunity to devise appropriate surveillance plans that may include enhanced screening for women at increased risk of breast cancer. Computerized analysis of mammographic parenchymal patterns may provide an objective and quantitative characterization and classification of these patterns, which may be associated with breast cancer risk. Computerized assessment of breast cancer risk based on the analysis of mammograms alone, or combined with epidemiologic risk factors (for example, age), may serve as an alternative to current existing clinical methods, which are costly and/or information-dependent, in predicting breast cancer risk.

As the best method for early detection of breast cancer, annual screening mammography has been recommended for women over 40 years of age (Ref. 25). Mammographic surveillance for women under age 40 years who are at very high risk of developing breast cancer, however, still remains an issue, since the benefit of screening women in this age group has not been proven. Women at high risk of developing breast cancer tend to develop breast cancer at a younger age (Ref. 26). Identification and close follow-up of these high-risk women may provide an opportunity for early breast cancer detection. Thus, computerized methods that are capable of assessing breast cancer risk may allow women and their physicians to devise an individualized surveillance plan that may include enhanced screening for women at high risk for early detection of breast cancer. These plans may lead to improvements in the overall efficacy of screening mammography for early detection of breast cancer. Further, knowledge of which women are at high risk of developing breast cancer has important implications in the study of breast cancer.

There are two widely used methods to measure risk: relative risk and absolute risk (Ref. 27). Relative risk is defined as the ratio of age-specific breast cancer incidence rate among women with specific risk factors to the incidence rate among women without known risk factors. Relative risk estimates are useful for measuring the relative magnitude of effect of a given risk factor as a population risk. However, relative risk estimates do not directly approximate the underlying probability of a diagnosis of breast cancer for an individual over time.

Absolute risk (or cumulative risk) is defined as the probability that a woman with given risk factors and given age will develop breast cancer over a defined time period. Absolute risk estimates give women a realistic and individualized estimate of the chance of developing cancer over various time horizons. An assessment of cumulative risk over different periods of time can help a woman understand the extent of her risk and therefore, can be useful in helping the woman and her doctor define an acceptable surveillance plan for the future.

For decades, it has been known that all breast cancers are genetic, i.e., the development of breast cancer is the result of alteration of chromosomal DNA through mutation or damage with the resultant loss of normal growth regulation (Ref. 28). Sporadic breast cancer results from somatic changes that are specific to the tumor cells, i.e., the epithelial cells of the breast, which are not found in other cells of the patient. Recent molecular studies demonstrate that breast cancer may be inherited (Refs. 29–31). In a landmark article published in 1990, King et al. used genetic linkage analysis to identify a gene named BRCA1 (breast cancer 1), which was found to be responsible for the breast cancer diagnosed in women who inherited a mutated form of the BRCA1 gene in all cells (germline mutation) at birth. Since then, four other genes responsible for breast cancer, including the BRCA2 (breast cancer 2) gene, have been identified (Ref. 32). In general, hereditary breast cancer appears earlier than purely sporadic breast cancer, because among women with inherited susceptibility, one of the cancer-causing mutations is present from birth. Thus, fewer somatic mutations specific to breast cancer cells need to occur.

It is estimated that women who inherit a mutated form of the BRCA1 gene have as much as a 20% risk of developing breast cancer by age 40 years, a 33%–73% risk of developing breast cancer by age 50 years, and an 56%–87% risk of developing breast cancer by age 70 years (Refs. 33, 34), which is about up to 8 times higher than the lifetime risk for the general population. The recent isolation of BRCA1 and BRCA2, and the acknowledgment that additional breast cancer susceptibility genes may exist, provides a molecular basis for counseling some high-risk women.

Although the evidence of familial aggregation of breast cancer suggests that there is an important hereditary component, there are many families in which breast cancer (familial breast cancer) has appeared more than once purely by chance and not as the result of inherited susceptibility. Studies show that truly hereditary breast cancers accounts only for 5%–10% of all breast cancers (Refs. 35, 36), and most breast cancers occur sporadically and are likely the result of random events on the cellular level. In addition to age, many factors have been identified to be related to breast cancer risk. Although, the basic mechanism underlying the association between breast cancer and these risk factors is not well understood. It has been recognized for some time that varying levels of endogenous and exogenous estrogens have been associated with the risk of developing breast cancer. Higher levels of endogenous hormones, in particular estrogens, are an important factor in the etiology of breast cancer (Refs. 37, 38).

TABLE 1

Selected factors for breast cancer risk.

| Factor | Comparison group | Approx. relative risk |
|---|---|---|
| Age | | |
| 40–44 | Age 25–29 | 16 |
| 50–54 | " | 28 |
| 60–64 | " | 44 |
| 70–74 | " | 56 |
| Western country | Japan | 5 |
| Family history of breast cancer | | |
| One affected first-degree relative | No affected first-degree relative | 1.4–3 |
| Two or more affected first-degree relatives | No affected first-degree relative | 4–6 |
| Early age (30 yrs old) of onset in affected relative | Age 50 | 2.6 |
| Reproductive history | | |
| Age at menarche, 11 | Age 16 | 1.3 |
| Age at first live birth | | |
| 20–24 | <20 | 1.3 |
| 25–29 | " | 1.6 |
| >=30, nulliparous | " | 1.9 |
| Age at menopause | | |
| After 55 | Age 45–55 | 1.5 |
| Before 45 | " | 0.7 |
| Evidence of breast pathology | | |
| Any benign disease | No biopsy or aspiration | 1.5 |
| Proliferative disease | " | 2 |
| Atypical hyperplasia | " | 2–4 |
| History of cancer in contralateral breast | No history of cancer | 5 |
| Percent dense parenchyma on mammography | | |
| 5%–24.9% | <5% dense regions | 1.7 |
| 25%–44.9% | " | 2.5 |
| 45%–64.9% | " | 3.8 |
| >65% | " | 4.3 |
| Exposures | | |
| Radiation, 100 rads | No special exposure | 3 |
| Alcohol, two drinks/day | Nondrinker | 1.7 |

From Gail MH, Benichou J. Assessing the risk of breast cancer in individuals. In deVita VT, Helman S, Rosenberg SA (eds): Cancer Prevention, Philadelphia, JB Lippincott; 1992, pp. 1–15.

Risk factors for breast cancer can be classified broadly as being of either personal or environmental origin. Personal risk includes aspects of individual biological histories, such as family history of breast cancer, reproductive history, menopausal status, and breast disease history. Environmental risk factors are exogenous influences, such as diet and exposure to environmental carcinogens. Table 1 lists selected factors that have a strong or well-established association with breast cancer. These factors were identified on the basis of large epidemiologic studies (Ref. 39).

Among these risk factors, age has been identified as the single most important risk factor for the development of breast cancer in women. The incidence of breast cancer increases with age. Studies show that diagnosis of breast cancer is rare before age 25 years (Ref. 40). The incidence of breast cancer increases rapidly between the ages of 25 and 44. Near the age of menopause, the rate of increase in incidence for successive age groups is slower compared with the observations in premenopausal women. In addition to age, risk factors such as family history of breast cancer, personal history of breast cancer, biopsy-confirmed benign proliferative breast disease, and age at first live birth and at menarche have been identified and have been used in clinical risk prediction models (Refs. 27, 39, 47) to estimate an individual's risk of developing breast cancer.

Increased mammographic density is another factor that has been found to be associated with an increased risk of breast cancer. It has been shown in several studies that women with increased mammographic parenchymal density are at a four- to six-fold higher risk over women with primarily fatty breasts (Refs. 41–46). At present, the reason for this increased risk is unclear. One possibility is that increased density reflects a larger amount of tissue at risk for developing breast cancer. Since most breast cancers develop from the epithelial cells that line the ducts of the breast, having more of this tissue as reflected by increased mammographic density may increase the chances of developing breast cancer.

In this study, the Gail and the Claus models were used to estimate individual risk over a woman's lifetime (up to 79 years old) and during the next 10 years of her lifetime, which are referred to as the lifetime risk and the 10-year risk of developing breast cancer. The Gail model (Ref. 48) was developed based on case-control studies involving 2,852 white women with incident breast cancer and 3,146 white controls selected from the Breast Cancer Detection Demonstration Project (BCDDP) population data. The risk factors used in the Gail model are age, age at menarche, age at first live birth, number of previous breast biopsies, number of first-degree relatives with breast cancer and history of biopsy with hyperplasia (Refs. 39, 48). These risk factors are broadly consistent with those selected from other large population-based studies (Ref. 39). Because the Gail model was developed from a database which includes only white women who tend to return for annual mammographic screening (Ref. 39), it is anticipated that this model would overpredict risk in younger, unscreened women since the BCDDP population had a higher prevalence of women with adverse risk factors than the general population (Refs. 39, 48).

The Claus model (Ref. 47) was derived from the Cancer and Steroid Hormone (CASH) Study, which was a multi-center, population-based, case-control study. The data consists of 4730 patients with histologically confirmed breast cancer, age 20–54 years, and 4688 control subjects. The control subjects were frequency-matched to patients according to geographic region and 5-year categories of age. The aim of the study conducted by Claus et al. differs from that of Gail et al. in that Claus et al. intended to address the issue of risk calculation solely for a subset of women who are at potentially high risk for breast cancer, i.e., women with a family history of breast cancer. For these women, it appears that the number and the type of relatives affected with breast cancer as well as the ages at onset of any affected relative may be the most important risk factors, more so than risk factors such as age at first live birth or age at menopause that are used in the Gail model. Claus et al. found in their data that risk of individuals increased as "age at onset" of their affected relatives decreased (Ref. 47). On the other hand, Gail et al. did not find, in their data, that age at onset was helpful in the prediction of risk once the number of relatives affected was considered (Refs. 39, 48).

Because the risk factors used in the Gail model are more consistent with those selected from other studies, the Gail model was able to be validated on other large databases. Validation studies (Refs. 49, 50) have shown that the Gail model predicts risk most accurately in women who undergo yearly mammographic screening and overpredicts risk for women who do not undergo yearly mammographic screening. Another validation study, which involved 109,413 women from the Nurses' Health Study, showed that the correlation coefficient between observed risk from the database and predicted risk from the Gail model was 0.67 (Ref. 50). These validation studies demonstrated that, for accurate estimation, the Gail and Claus models should be applied only to a population similar to those from which the models were derived.

With the increasing awareness of breast cancer risk and the benefit of screening mammography, more women in all risk categories are seeking information regarding their individual breast cancer risk. The need exists for primary care clinicians to be able to assess an individual's risk of developing breast cancer and offer an appropriate surveillance program for each individual. Identification and close surveillance of women who are at high risk of developing breast cancer may provide an opportunity for early cancer detection.

Breast cancer risk assessment is an emerging service which includes determination of risk, recommendations for surveillance, and counseling for women at elevated risk. Currently, several prediction models based on large epidemiologic studies (Ref. 27) have been developed to predict risk using known risk factors such as a woman's age, her family and personal histories of breast cancer, and gynecological information. Among them, the Gail model and the Claus model are the most commonly used for prediction of an individual's breast cancer risk (Ref. 51). These models are used by clinicians for counseling women who are seeking information regarding their individual breast cancer risk. The Gail model was used to identify women at high risk for the entry to the Tamoxifen Prevention Trial. Recently, Offit and Brown (Ref. 27) reviewed four major models of risk prediction and provided a comparison of the different models. Since each of these models was derived with a different study design and used different factors to calculate risk, risk estimates for a given individual obtained from each of the models differed slightly. It was anticipated and confirmed that these models, which use a few selected risk factors, only predict risk accurately for the populations similar to those from which the models were developed (Refs. 39, 47, 48, 49, 50, 52). Clinicians have been instructed to select models carefully since each of these models was designed based on a particular population. Further, the risk predicted from these models must be justified according to clinical observations since information such as a positive result from a DNA test for the BRCA1/BRCA2-mutation supersedes routine projections from a model (Refs. 51, 52). Nevertheless, the models provide an epidemiologic basis for risk prediction and serve as guidelines for counseling patients until more refined predictions based on molecular characterization or other methods become available.

Over the past twenty years, the association of breast cancer risk with mammographic parenchymal patterns has been investigated. In 1976, Wolfe first described an association between risk for breast cancer and different mammographic patterns (Ref. 53). He described four patterns of breast parenchyma (N1, P1, P2, and DY) associated with different risk levels of developing breast cancer. An N1 (lowest risk) pattern indicates a breast in which the breast is composed entirely of fat tissue. P1 (high risk) and P2 (high risk) patterns refer to increasing ductal prominence (a P1 pattern consists of ducts occupying less than 25% of the breast and a P2 pattern consists of ducts occupying more than 25% of the breast). A DY pattern (highest risk) refers to a breast which is largely occupied by diffuse or nodular densities. Many investigators have used Wolfe patterns to classify the mammographic appearance of breast parenchyma for risk prediction (Ref. 54). Others have used qualitative or quantitative estimates of the proportion of the breast area (percent density) that mammographically appears dense to assess the associated breast cancer risk.

Since Wolfe's work, interest in the possible association of mammographic parenchymal patterns with breast cancer has varied (Refs. 55–57). Wolfe's initial reports were landmark studies in this field. However, the results provoked various criticisms, for example, possible bias in the results due to the "masking" effect. Studies showed that breast cancer was most easily detected by mammography in fatty breasts and was most difficult to detect in breasts with dense parenchyma. Thus there were more cancers missed by mammography in women with dense breasts (Ref. 58). The hypothesis of the "masking effect" (Ref. 55) said that the observed greater risk of breast cancer in women with dense breasts was due to the fact that these missed cancers in the dense breast at the initial classification declared themselves on subsequent follow-up.

Several groups (Refs. 44, 59) have conducted experiments to examine the masking hypothesis. Whitehead et al. (Ref. 59) examined the masking hypothesis by using data from the Breast Cancer Detection and Demonstration Project (BCDDP). They found that the masking of cancer did occur in breasts with dense parenchyma. However, their results showed that the effect of the masking on estimation of breast cancer risk was small. They concluded that women with dense breasts have two disadvantages: (1) they were at increased risk of developing breast cancer, and (2) cancers occurring in dense breast parenchyma were more difficult to detect.

During the time of this controversy, many investigators studied the relationship between the mammographic patterns and breast cancer risk using the Wolfe method or percent density methods. Considerable variations were observed in reported results. In 1992, Warner et al. (Ref. 54) carried out a meta-analysis using 35 publications to examine the effect of different methods on the assessment of breast cancer risk. They grouped the studies according to their designs and methods used, and determined the magnitude of the risk of breast cancer associated with mammographic density for the studies in each group. They found that the estimated relative risk of developing breast cancer depended on the methods that were used to classify mammographic patterns and ranged from 0.53 to 5.19. Based on the meta-analysis, they concluded that women with dense breasts have an increased risk of breast cancer relative to those with fatty breasts.

While visual assessment of mammographic patterns has remained controversial due to the subjective nature of human assessment (Ref. 60), computer vision methods can yield objective measures of breast density patterns. Computerized techniques have been investigated to quantitatively evaluate mammographic parenchyma and identify women that are at risk of developing breast cancer. Computerized density analysis of mammographic images has been investigated by various investigators including Magnin et al. (Ref. 61), Caldwell et al. (Ref. 62), Taylor et al. (Ref. 63), Tahoces et al. (Ref. 64), and Byng et al. (Refs. 65, 66).

Magnin et al. (Ref. 61) tried to classify mammograms into four categories (Wolfe patterns) using texture parameters extracted from co-occurrence matrices, the spatial gray level dependence method (SGLDM), and the gray level difference method (GLDM). They claimed that their result was inconclusive because a limited number of cases (27 mammograms) were used and the quality of the images used in the study was poor (Ref. 61). Caldwell et al. (Ref. 62) used fractal dimension analysis to classify mammograms into the four patterns described by Wolfe, yielding 84% agreement with that of radiologists. Tahoces et al. (Ref. 64) investigated the ability of linear discriminant analysis to quantify Wolfe patterns by merging texture measures obtained from a Fourier transform method, local contrast analysis, and gray-level distribution. Their results showed that agreement (22%–77%) among radiologists and the computer classification varied depending on the Wolfe patterns. Taylor et al. (Ref. 63) used a local skewness measure to separate fatty and dense breasts, yielding 85% classification accuracy for 106 mammograms. Byng et al. (Refs. 65, 67) investigated a semi-automated interactive thresholding technique based on visual assessment and computerized texture analysis (a local skewness measure and fractal dimension analysis) to quantify the percent density of breasts. Their results showed that computerized assessment of mammographic density using the texture measures (r=−0.60) correlated well with the visual assessment (subjective classification) of the projected area of mammographically dense tissue. Furthermore, they showed that increased mammographic density was associated with an increased relative risk by a factor of 2 to 4. Their results also showed that the relative risk estimates obtained using the two computer-extracted texture measures were not as strong as those from their subjective mammographic classification method.

Development of a computerized method to automatically extract features that characterize mammographic parenchymal patterns and relate to breast cancer risk would potentially benefit women seeking information regarding their individual breast cancer risk.

Computerized methods for measuring breast structure that may be used together with clinical measures of risk for use in quantitatively characterizing the breast parenchyma and risk of cancer (Ref. 68) have been developed. Mammographic films for 505 women who are at low risk, moderate risk, and high risk, including 380 with no cancer, 32 with BRCA1/BRCA2 gene mutation, and 93 with breast cancer have been digitized. For each case, information such as subjects' age, age at menarche, age at first live birth and number of first-degree and second-degree relatives having breast cancer and their age onset was tabulated, and the Claus and Gail models were calculated for both lifetime and ten-year risk. The mammograms were digitized into an approximately 2048 by 2048 matrix with 10-bit quantization. After the radiographic images were in digital format, regions of interest (ROIs) were selected from regions within the breasts (behind the nipple, and within dense and fatty portions) in order to determine the variation of texture within an individual's breast image. The ROIs served as the input to the computerized texture analysis scheme.

Computer-extracted mammographic features such as skewness, RMS variation from Fourier analysis, coarseness, and contrast were used to characterize percent denseness of the breast or the heterogeneity (diffuse) patterns in the dense portions of the breast (Ref. 68). Three different approaches to relate mammographic patterns, as characterized by these computer-extracted features, to the risk of developing breast cancer, i.e., (a) presence of biomarkers (BRCA1/BRCA2 gene testing) of risk, (b) the actual onset of cancer, and (c) current clinical indicators of risk (such as the Gail model) were investigated. In these studies, mammographic parenchymal patterns of these three groups of high-risk women were analyzed in comparison with those from a group of low-risk women. The low-risk group includes women with no family history of breast/ovarian cancer and no prior history of breast cancer and benign breast disease. In addition, these women have a less than 10% lifetime risk of developing breast cancer based on the Gail model. In the first approach, stepwise linear discriminant analysis (LDA) was employed to identify computer features that distinguish mammographic patterns between BRCA1/BRCA2 mutation carriers and low-risk women. In the second approach, stepwise linear logistic regression was investigated to identify computer features that distinguish mammographic patterns between women with and those without breast cancer. In the third approach, stepwise linear regression was used to identify computer features that correlate with clinical risk models (the Gail and Claus models). Quantitative analyses of mammographic patterns, from all three groups, indicate that women at high risk tend to have dense breast with coarse and low-contrast texture patterns. These results are reported below.

First Approach: Mammographic Characteristics of BRCA1/BRAC2 Mutation Carriers vs. Low-risk Women In the first approach, computer analysis was performed to analyze mammographic patterns of mutation carriers in comparison with those of low-risk women. Thirty-two BRCA1/BRCA2 mutation carriers and 142 low-risk women were included in this study. Stepwise linear discriminant analysis was performed to select a set of computer features that distinguish mammographic patterns between BRCA1/BRCA2 mutation carriers and low-risk women.

To rule out the possible bias due to the difference in age distribution, the mammographic patterns of 32 BRCA1/2 mutation carriers and 64 low-risk women who were randomly selected and age-matched to the 32 mutation carriers at a 5-year interval were analyzed. Mammographic patterns as characterized by the selected computer features (skewness, coarseness, and contrast), shown in FIGS. 4(a) and 4(b), indicate that the mutation carriers tend to have more dense breast tissue than do the low-risk women, as indicated by the lower (negative) values of skewness. In addition, the mammographic patterns of the mutation carriers tend to be coarser in texture and lower in contrast than do those of the "low risk" cases. The distribution of the discriminant scores from the LDA using the selected computer features is shown in FIG. 5. ROC (receiver operating characteristic) analysis was performed to evaluate the ability of individual features and linear discriminant analysis in differentiating between the mutation carriers and low-risk women. The separation in the discriminant scores between the mutation carriers and low-risk women yielded Az values of 0.92 and 0.91 for the entire database and the age-matched group.

Second Approach: Mammographic Characteristics of Women with Cancer vs. Women Without Cancer In the second approach, computer analysis was performed to analyze mammographic patterns of 93 women with unilateral breast cancer in comparison with those of the 142 low-risk women. The CC views of the contralateral breast of the cancer cases at the time of the diagnosis (not from previous exams) and the left CC views from the low-risk cases were used for the computerized analysis. Stepwise linear logistic regression was employed to identify computer features that distinguish mammographic patterns between women with and those without breast cancer in the entire database. In addition, mammographic patterns of women with and without cancer in an age-matched group were analyzed. The age-matched group consisted of 30 cancer cases and 60 cancer-free women with ages ranging from 35 years to 54 years, whereas the entire database consisted of 93 cancer cases with ages ranging from 39 years to 84 years and 142 cancer-free women with age ranging from 35 year to 54 years. FIGS. 6(a) and 6(b) shows the distribution of women with and without breast cancer from the age-matched group in terms of the selected computer features. Again, it was found that high-risk women, i.e., the women with breast cancer in this analysis, tend to have dense breasts and coarse with low-contrast mammographic patterns.

Further, the effect of these computer features on the risk of developing breast cancer was quantified by odds ratios (OR), an estimate of relative risk. The odds ratios and their 95% confidence intervals for individual features calculated from the logistic regression analysis are listed along with their corresponding p-values in Table 2. These odds ratios suggest that increased mammographic density as indicated by an increase in the RMS variation is associated with an increased risk of developing breast cancer (OR=1.1). In addition, change in mammographic patterns as indicated by an increase in the texture measures of coarseness and contrast is associated with an increase (OR=1.74) and a decrease (OR=0.33) in breast cancer risk, respectively. The odds ratios were also calculated for the selected features based on the analysis of women in the age-matched group (Table 3). It should be noted that the factor that is matched could not be evaluated in terms of its relationship to outcome. Overall, the results show that the computer-extracted features and age are significant risk factors for breast cancer, as indicated by the corresponding p-values listed in Tables 2 and 3.

TABLE 2

Odds ratios (ORs) calculated using the entire database.

| Features | OR | [95% Conf. Interval] | p-value |
|---|---|---|---|
| Age | 1.52 | [1.31, 1.75] | 0 |
| RMS | 1.1 | [1.01, 1.20] | 0.02 |
| Coarse* | 1.74 | [1.23, 2.41] | 0.001 |
| Contrast* | 0.33 | [10.20, 0.56] | 0 |

Note:
A one-unit increase for features indicted with* corresponds to 0.0001.

TABLE 3

Odds ratios (ORs) calculated using the age-matched group.

| Features | OR | [95% Conf. Interval] | p-value |
|---|---|---|---|
| Skewness | 0.36 | [0.13, 0.99] | 0.049 |
| Coarse* | 1.7 | [1.22, 2.37] | 0.002 |
| Contrast* | 0.44 | [0.26, 0.74] | 0.002 |

Note:
A one-unit increase for features indicted with* corresponds to 0.0001.

Third Approach: Mammographic Characteristics of Women at High Risk vs. Women at Low Risk In the third approach, mammographic patterns of women at high risk of developing breast cancer from the general population in comparison with those of low-risk women were analyzed. In total, 341 cancer-free cases were analyzed. Their ten-year risk (risk of developing breast cancer in the next 10 years) and lifetime risk (risk of developing breast cancer up to age 70) were estimated from both the Gail and Claus models. Based on the risk as estimated from the Gail and Claus models, 49 of 341 cases are determined as high-risk; 164 are determined as moderate-risk; and 142 are determined as low-risk. Stepwise linear regression analysis was employed to select features that correlate strongly with the risk. Linear regression analysis on the selected computer-extracted feature was performed to predict the risk as estimated from the Gail and Claus models. The relationship between these computer features and the risk of developing breast cancer was indicated by the coefficients from the linear regression model listed in Table 4. Listed also in Table 4 are the correlation coefficients (r) between the risk predicted from the regression model and the observed risk (estimated from Gail or Claus model).

The association between individual mammographic features and risk as estimated from the Gail or Claus model indicates that women with dense breasts (negative sign for skewness), and coarse (positive sign for coarseness) and low contrast (negative sign for contrast) mammographic patterns tend to have a high risk of developing breast cancer. In addition, the 10-year risk increases as age increases, whereas the lifetime risk decreases as age increases. Results from our preliminary study showed that the performance (r=0.41~0.57) of the computerized method using mammographic features and age in predicting breast cancer risk is comparable to that achieved between the Gail and Claus models among themselves (r=0.61 for 10-year risk and r=0.60 for lifetime risk) and seen in the Nurse's Health Study (r=0.67).

TABLE 4

Regression coefficients and correlation coefficients

| | Skewness | Coarseness | Contrast | Age | r | p-value |
|---|---|---|---|---|---|---|
| Gail model | | | | | | |
| lifetime risk % | −0.014 | +77.4 | −97.4 | −0.002 | 0.41 | <0.0001 |
| 10-year risk % | −0.004 | +34.5 | −38.3 | +0.002 | 0.41 | <0.0001 |
| Claus model | | | | | | |
| lifetime risk % | −0.034 | +57.6 | −255.1 | −0.002 | 0.55 | <0.0001 |
| 10-year risk % | −0.014 | +28.9 | −97.3 | +0.004 | 0.57 | <0.0001 |

To evaluate the importance of these mammographic features, the contribution of these computer-extracted features to risk prediction in terms of percent increase in the prediction power ($R2$) was assessed under two conditions: 1) when age was used alone and 2) when the mammographic features were added. The addition of any features to the regression model increases the squared correlation coefficient, $R2$. The increase in $R2$ measures the additional worth of the added features. Thus, the increase in $R2$, when the mammographic features are added to the regression model, quantifies the additional contribution of computer-extracted features to risk prediction. The inclusion of the mammographic features to the regression models increased the prediction power ($R2$) from 0.08 and 0.16 (age alone) to 0.17 and 0.32 at statistically significant levels, yielding an increase of 113% and 100% in R2 for the ten-year risks as estimated from the Gail and Claus models, respectively. The relative increases of 113% and 100% in R2 for the ten-year risks as estimated from the Gail and Claus models, respectively, indicate that the mammographic features contributed as much as age in the prediction of breast cancer risk, as estimated from the Gail and Claus models. It should be noted that age is the most important single risk factor for breast cancer.

Overall, the above studies using three different approaches demonstrate the association between computerized radiographic markers and breast cancer risk, and their significant contribution in breast cancer risk prediction.

SUMMARY OF THE INVENTION

Accordingly, an object of the present invention is to provide a method, system, and computer program product for analyzing lesions in medical images using risk information.

Another object of the present invention is to provide a method, system, and computer program product for analyzing lesions in medical images using computer-extracted risk information.

A further object of the present invention is to provide a method, system, and computer program product for distinguishing between diseased and non-diseased lesions in medical images using computer-extracted risk information.

Another object of the present invention is to provide a method, system, and computer program product that performs computerized differential diagnosis of medical images using computer-extracted risk information.

Another object of the present invention is to provide a method, system, and computer program product for analyzing lesions in medical images using computer-extracted risk information for assessment of a specific population of subjects.

Another object of the present invention is to provide a method, system, and computer program product for analyzing lesions in medical images using computer-extracted risk information for the computer-assisted interpretation of medical images, and output to the radiologist/physician the computer analysis of the medical images.

These and other objects of the present invention are achieved by providing a method, system, and computer program product for calculating a disease assessment by analyzing a medical image, comprising: (1) extracting at least one lesion feature value from the medical image; (2) extracting at least one risk feature value from the medical image; and (3) determining the disease assessment based on the at least one lesion feature value and the at least one risk feature value.

In one embodiment, the step of determining the disease assessment comprises calculating a quantitative measure of malignancy as the disease assessment by applying the at least one lesion feature value and the at least one risk feature value to a classifier.

In a second embodiment, the step of determining the disease assessment comprises: (1) calculating a quantitative measure of risk by applying the at least one risk feature value to a first classifier; (2) calculating a quantitative measure of malignancy by applying the at least one lesion feature value to a second classifier; and (3) multiplying the quantitative measure of malignancy by the quantitative measure of risk to obtain the disease assessment.

In a third embodiment, the step of determining the disease assessment comprises: (1) determining a quantitative measure of risk by applying the at least one risk feature value to a first classifier; (2) classifying the quantitative measure of risk as high risk if the quantitative measure of risk exceeds a predetermined threshold risk value; (3) determining the disease assessment by applying the at least one lesion feature value to a second classifier, if the quantitative measure of risk is classified as high risk; and (4) determining the disease assessment by applying the at least one lesion feature value to a third classifier, if the quantitative measure of risk is not classified as high risk.

Further, the present invention provides a method, system, and computer program product for extracting the at least one lesion feature value, comprising: (1) locating a lesion in the medical image; (2) extracting segmented image data of a portion of the medical image corresponding to the lesion; and (3) extracting the at least one lesion feature value from the segmented image data.

In addition, the present invention provides a method, system, and computer program product for extracting at least one risk feature value, comprising: (1) locating a region of interest (ROI) in the medical image corresponding to a parenchymal region; and (2) extracting the at least one risk feature value from the ROI.

In addition, the present invention provides a method, system, and computer program product for training a classifier in relation to the at least one lesion feature value and the at least one risk feature value obtained from a set of previously obtained medical images based on a measure of malignancy associated with the previously obtained medical images.

Preferred embodiments of the present invention provide a method and system that employ a lesion characterization module and a risk assessment module for characterizing the lesion and the environment local and distal to the lesion in question. A specific example presented here includes a computerized method for the characterization of mammographic lesions combined with a computerized method for the assessment of the breast parenchymal pattern on mammograms, resulting in improved characterization of lesions for specific subpopulations. A computerized risk-modulated analysis system for medical images combines the benefits of computerized lesion analysis with information of the lesion surround (local and distal environment). Use of such a system allows focusing and optimizing the computer output for specific populations.

In addition, computer-aided diagnosis is improved by merging computer-extracted lesion features with computer-extracted parenchyma features, and by the investigation of such features across different populations and risk categories.

According to other aspects of the present invention, there is provided a novel system implementing the methods of the present invention, and novel computer program products that, upon execution, cause the computer system to perform the method of the present invention.

BRIEF DESCRIPTION OF THE DRAWINGS

A more complete appreciation of the invention and the many of the attendant advantages thereof will be readily obtained as the same becomes better understood by reference to the following detailed description when considered in connection with the accompanying drawings, in which like reference numerals refer to identical or corresponding parts throughout the several views, and in which.

DETAILED DESCRIPTION OF THE PREFERRED EMBODIMENTS

Figure 1A:
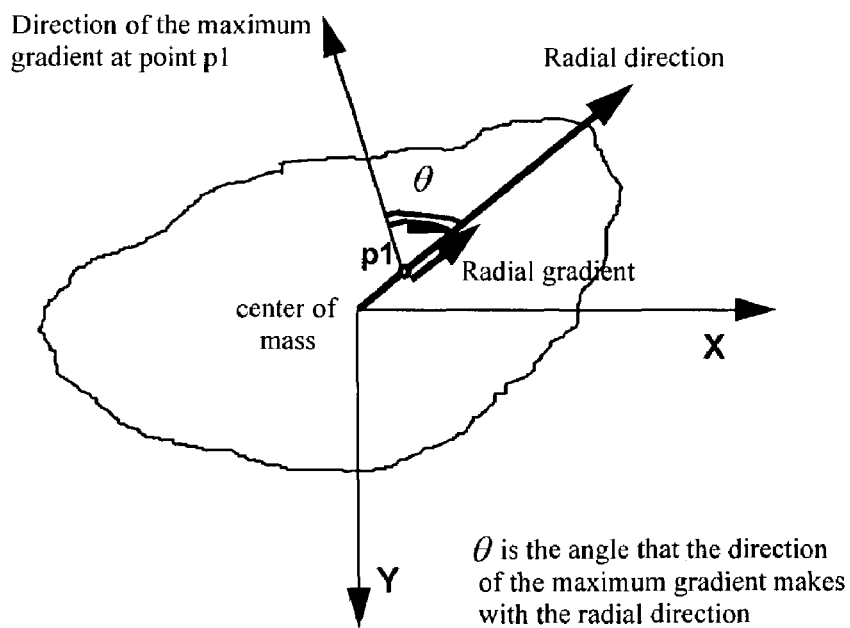
FIG. 1A defines the radial angle as the angle between the direction of the maximum gradient and its radial direction.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The invention relates generally to the field of computer-aided diagnosis in the detection, characterization, diagnosis, and assessment of normal and diseased states (including lesions) in general and specific subpopulations. The system of the present invention employs a lesion characterization module and a risk assessment module for characterizing the lesion and the environment local and distal to the lesion in question. The specific embodiment presented here includes a computerized method for the characterization of mammographic lesions combined with a computerized method for the assessment of the breast parenchymal pattern on mammograms. The use of a combination of these features can result in improved characterization of lesions for specific subpopulations of women.

A computerized risk-modulated analysis system for medical images combines the benefits of computerized lesion analysis with information of the lesion's surroundings (local and distal environment). It is expected that use of such a system will improve the use of computerized image analysis in medical imaging by focusing and optimizing the computer output for specific populations. In addition, it is expected that methods of computer-aided diagnosis will improve by the merging of computer-extracted lesion features with computer-extracted parenchyma features and by the investigation of such features across different populations and risk categories.

While the inventors have investigated various computer-extracted features of lesions (and their relationship to likelihood of malignancy), and various computer-extracted characteristics of parenchyma pattern (and their relationship to breast cancer risk), the combination of those two sets of features will aid the determination of (1) the anatomical assessment of tumor growth (that is, do tumors grow at a specific rate due to the type of tumor or due to its environment (parenchyma type) or both?), and (2) the manner in which computerized analyses of lesions vary across patient populations and risk categories.

Figure 7:
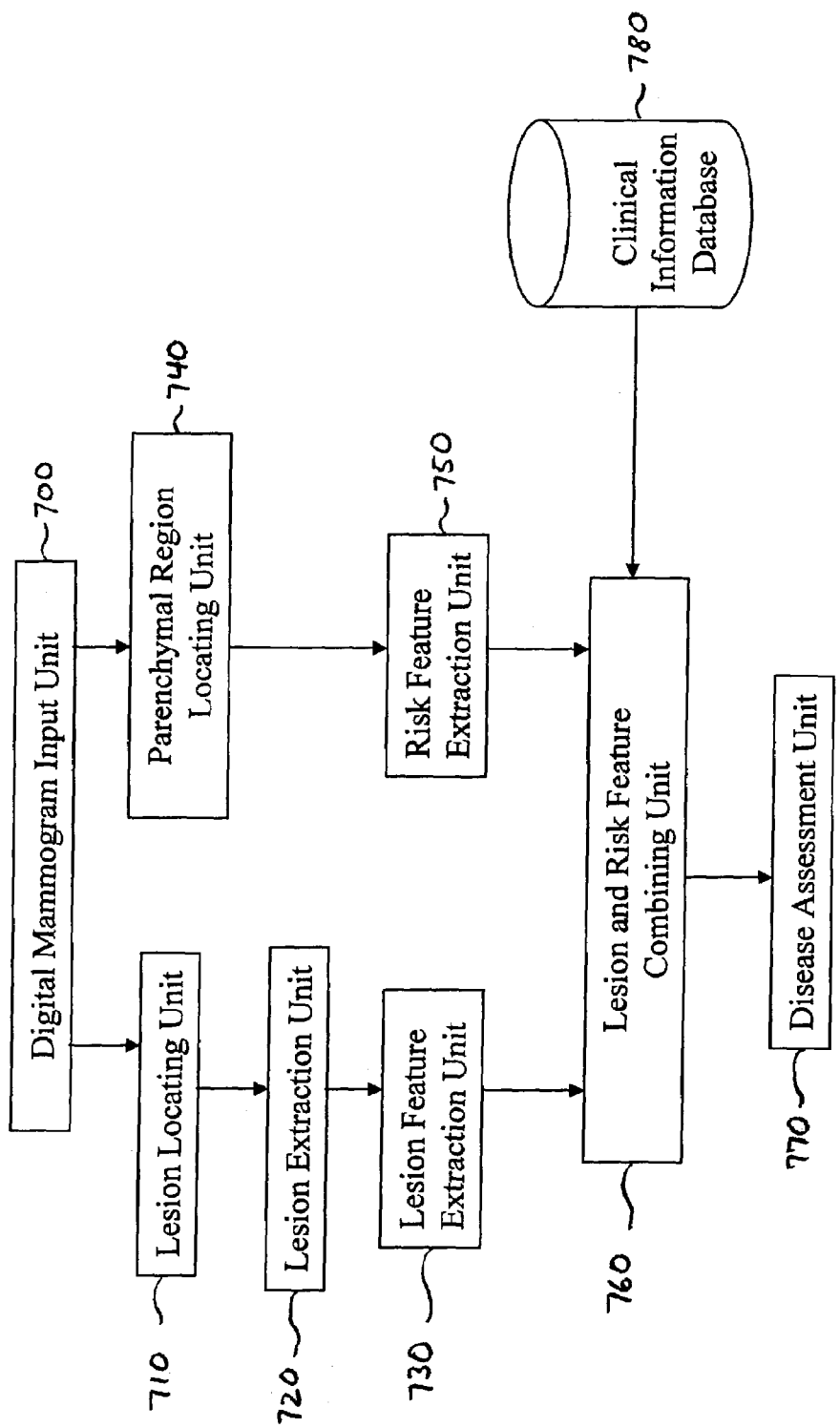
FIG. 7 shows an exemplary method that characterizes lesions on medical images using calculated risk estimates.

Referring now to the drawings, and more particularly to FIG. 7 thereof, a schematic diagram of a preferred system that takes as input a digital mammogram and outputs information regarding potential lesion sites, likelihoods of malignancy, and an assessment of risk of future breast cancer is illustrated. In FIG. 7, a digital mammogram is input into the Digital Mammogram Input Unit 700 and used as input to the Lesion Locating Unit 710 and the Parenchymal Region Locating Unit 740. The Lesion Locating Unit 710 uses various techniques (described below) to locate at least one lesion site within the digital mammogram. The Lesion Extraction Unit 720 uses the at least one lesion site located by the Lesion Locating Unit 710 to extract at least one lesion. Next, the Lesion Feature Extraction Unit 730 calculates various lesion feature values associated with each lesion extracted by the Lesion Extraction Unit 720.

Similarly, the Parenchymal Region Locating Unit 740 locates a region of interest within the parenchymal region of the digital mammogram in order to determine various risk features. The risk features, which are calculated by the Risk Feature Extraction Unit 750, are described in more detail below with reference to the methods illustrated in FIGS. 8A–8C.

The lesion and risk feature values determined by the Lesion Feature Extraction Unit 730 and the Risk Feature Extraction Unit 750, respectively, as well as data from the Clinical Information Database 780 are input into the Lesion and Risk Feature Combining Unit 760, which has been trained to classify the lesion as malignant or benign. The Disease Assessment Unit 770 determines an overall assessment of risk from the lesion, including localization, likelihood of malignancy, and cancer stage using the output of the Lesion and Risk Feature Combining Unit 760. Note that the Lesion and Risk Feature Combining Unit 760 could include a linear discriminant, an artificial neural network, or another appropriate classifier.

As discussed above, in the various embodiments implementing the system and methods of the present invention, various features used to assess the disease condition are either determined manually or computer extracted. The features that may be used for characterizing lesions and the parenchyma, which are computed by the Lesion Feature Extraction Unit 730 and the Risk Feature Extraction Unit 750, respectively, are described in more detail below.

Computer-Extracted Features to Characterize Lesions

Radiographically, mass lesions can be characterized (Refs. 7, 9) by, for example:

Lesion Feature 1: degree of spiculation (spiked versus rounded),

Lesion Feature 2: margin definition (margin sharpness);

Lesion Feature 3: shape;

Lesion Feature 4: density (determined using average gray level, contrast, and texture);

Lesion Feature 5: homogeneity (texture);
Lesion Feature 6: asymmetry; and
Lesion Feature 7: temporal stability.

Figure 1B:
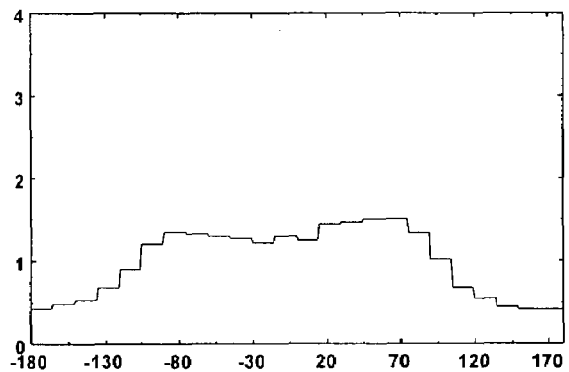
FIG. 1B illustrates the normalized cumulated edge-gradient distributions for spiculated masses.
Figure 1C:
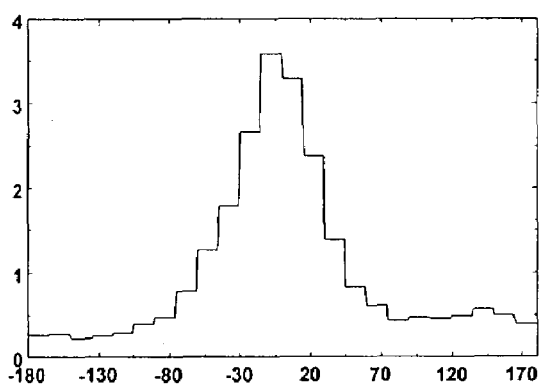
FIG. 1C illustrates the normalized cumulated edge-gradient distributions for circular masses where a FWHM (full width at half max) value is extracted from the plots to yield the spiculation measure.
Figure 2:
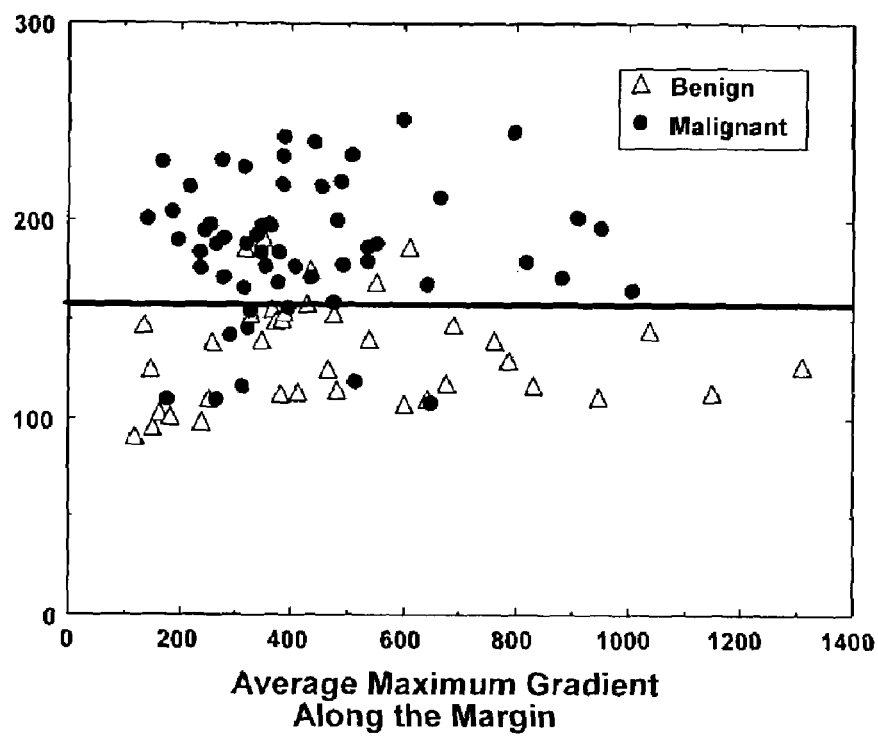
FIG. 2 shows the relationship between measures of spiculation and margin definition for malignant and benign mammographic masses.
Figure 3:
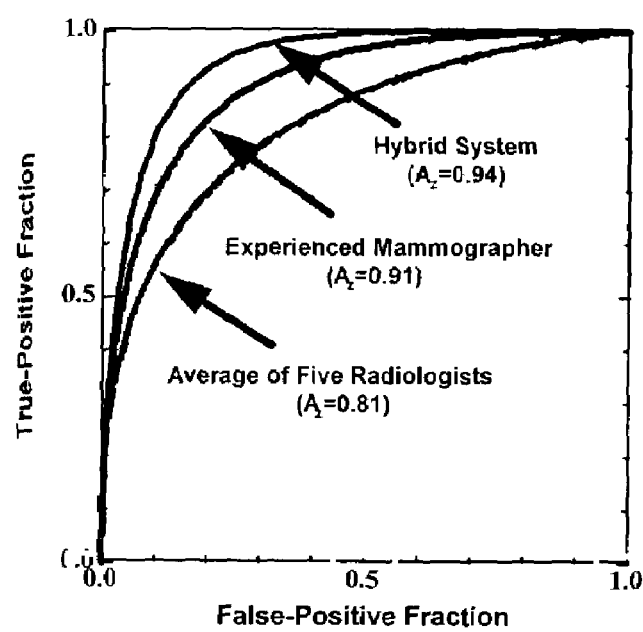
FIG. 3 shows the performance of the computerized mass analysis method as compared to that of an experienced mammographer and average radiologists in the task of distinguishing between malignant and benign breast mass lesions.
Figure 4A:
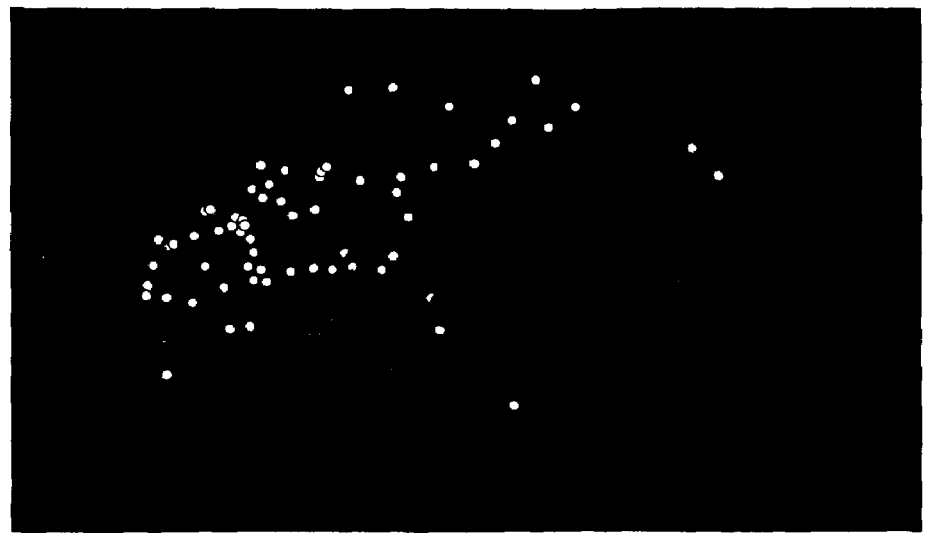
FIGS. 4A and 4B show distributions of mammographic patterns in terms of computer-extracted features for, respectively, mutation cases and low-risk women from an age-matched group.
Figure 4B:
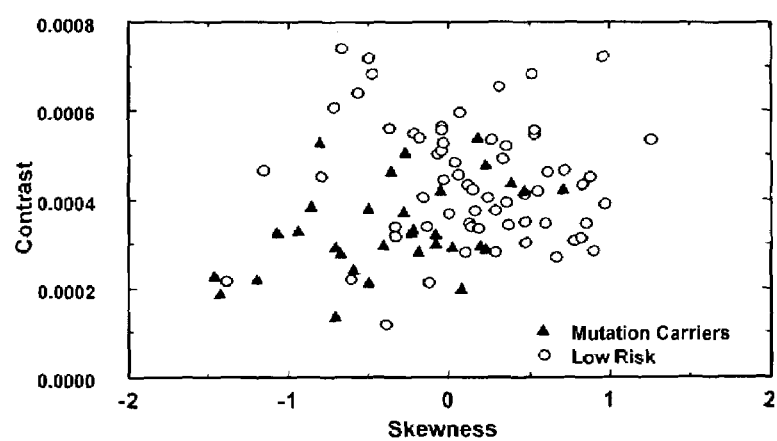
Figure 5:
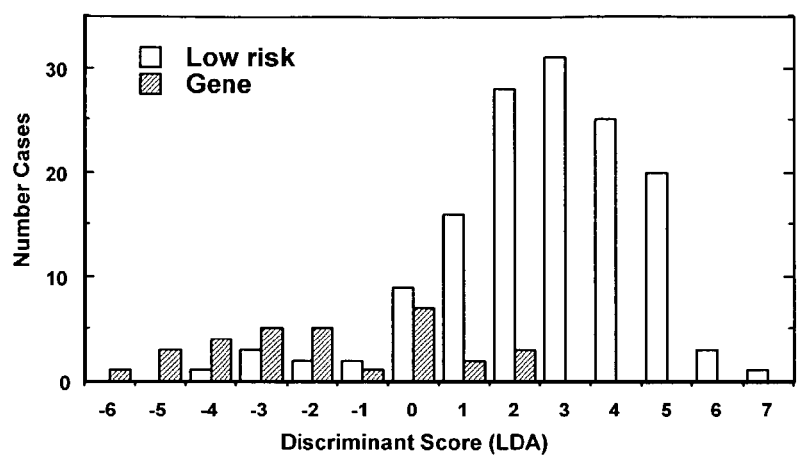
FIG. 5 shows a distribution of discriminant scores of the mutation carriers and low-risk women from the entire database.
Figure 6A:
FIGS. 6(a) and 6(b) show mammographic patterns in terms of computer-extracted features for women with and without breast cancer from the age-matched group.
Figure 6B:
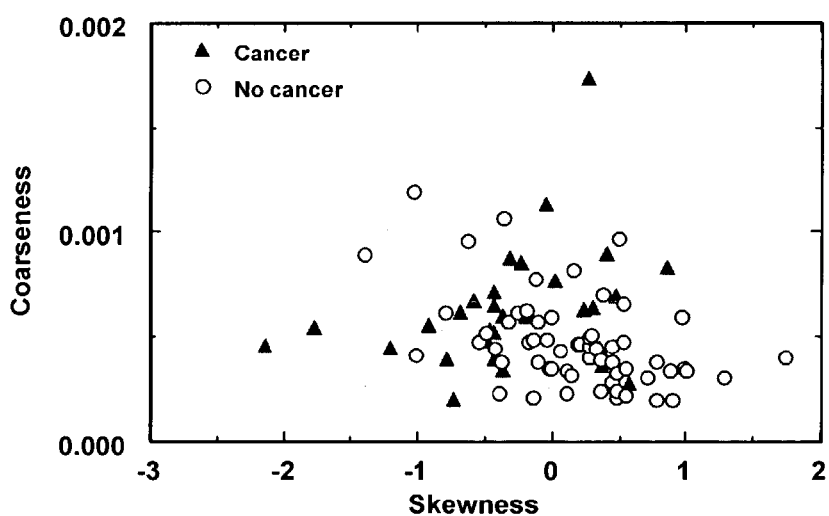

Mass lesions from mammograms may be characterized using the present inventors' earlier work (Refs. 17, 21, 23, 24), in which a characterization scheme based on the degree of spiculation is determined from a cumulative edge gradient histogram analysis in which the gradient is analyzed relative to the radial angle (See FIG. 1). The mass is first extracted from the anatomic background of the mammogram using automatic region-growing techniques (Ref. 17). Extracted features are then obtained using cumulative edge-gradient histogram analysis. In the cumulative edge-gradient analysis, the maximum gradient and angle of this gradient relative to the radial direction is calculated. FIGS. 1A–1C illustrate the calculation of the FWHM (full width at half max) value from the cumulative gradient orientation histogram for a spiculated mass and a smooth mass. Note that here the spiculation feature (based on the radial direction) is used in distinguishing between spiculated lesions and round lesions. Also, the average gradient along the margin of a mass is calculated to describe the sharpness of the margin. Higher values indicate a sharper margin, and thus a higher likelihood that the lesion is benign.

In addition, a radial gradient index (normalized radial gradient) (Refs. 21, 69) that describes the circularity and density characteristics of a lesion is calculated as $$RGI = \frac{\sum_{P \in L} \cos\varphi \sqrt{D_x^2 + D_y^2}}{\sum_{P \in L} \sqrt{D_x^2 + D_y^2}}$$

where:
RGI is a radial gradient index that is normalized to take on values between −1 and +1,
P is an image point,
L is the detected lesion excluding the center part,
$D_x$ is the gradient in the x-direction,
$D_y$ is the gradient in the y-direction, and
$\phi$ is the angle between the gradient vector and the connection line from the center point to a neighbor point.

Although the radiographic density of a mass may not be by itself as powerful a predictor in distinguishing between benign and malignant masses as margin features, taken with those features, density assessment can be extremely useful. The evaluation of the density of a mass is of particular importance in diagnosing circumscribed, lobulated, indistinct, or obscured masses that are not spiculated.

In order to assess the density of a mass radiographically, three density-related measures (average gray level, contrast, and texture measure) that characterize different aspects of the density of a mass are used. These measures are similar to those used intuitively by radiologists. Average gray level is obtained by averaging the gray level values of each point within the grown region of a mass. Contrast is the difference between the average gray level of the grown mass and the average gray level of the surrounding fatty areas (areas with gray-level values in the lower 20% of the histogram for the total surrounding area). Texture is defined here as the standard deviation of the average gradient within a mass and is used to quantify patterns arising from veins, trabeculae, and other structures that may be visible through a low-density mass, but not through a high-density mass. A mass of low radiographic density should have low values of average gray level and contrast, and a high value of the texture measure, whereas a mass of high radiographic density should have high values of average gray level and contrast, and a low value of the texture measure.

In a study demonstrating application of the present invention, ROIs (regions of interest) were selected from the central breast region behind the nipple because they usually include the densest parts of the breast. However, it should be noted that computer-extracted features that characterize the parenchyma can be obtained from any part of the breast. In this study, a constant ROI size was used for all breast images regardless of breast size.

In an exemplary embodiment of the present invention, fourteen risk features were extracted from each of the selected ROIs to quantify mammographic parenchymal patterns (Ref. 68):

Risk Features 1–7 (based on the absolute values of the gray levels):
1. maximum gray level of the ROI (MAX),
2. minimum gray level of the ROI (MIN),
3. average gray level of the ROI (AVG),
4. gray level yielding 5% of area under ROI histogram (5% CDF),
5. gray level yielding 30% of area under ROI histogram (30% CDF),
6. gray level yielding 70% of area under ROI histogram (70% CDF),
7. gray level yielding 95% of area under ROI histogram (95% CDF), Risk Features 8–10 (based on gray-level histogram analysis):
8. Balance, based on 5% and 95% cumulative distribution functions (CDFs) (Balance 1)
9. Balance, based on 30% and 70% cumulative distribution functions (CDFs) (Balance 2)
10. Skewness Risk Features 11–12 (based on Fourier analysis):
11. Coarseness (COS)
12. Contrast (CON)

Risk Features 13–14 (based on spatial relationship among gray levels within ROI):
13. Root mean square (RMS) variation of power spectrum
14. First moment of power (FMP) spectrum Features based on the absolute gray level values include the maximum, minimum, average gray level, and various gray-level thresholds that partition an ROI into light and dark binary regions. The gray-level thresholds which yield 5%, 30%, 70%, and 95% of the area under the gray-level histogram of an ROI cumulative distribution function (CDF) are calculated. Radiographically, the breast consists mainly of two component tissues: fibroglandular tissue and fat. Regions of brightness in mammography associated with fibroglandular tissue are referred to as mammographic density. These features are used as a means to quantify indirectly the brightness of the selected region, which may yield information regarding the denseness of the region.

A dense ROI tends to have more pixels with high gray level values (low-optical density) yielding a gray-level histogram skewed to the left. A fatty ROI tends to have more pixels with low gray level values (high-optical density) yielding a gray-level histogram skewed to the right. Features such as skewness and balance (defined below) of a histogram can be used to quantify the ratio of pixels with high gray level values to those with low gray level values, thereby approximating the local tissue composition (fibroglandular tissue vs. fat). A dense ROI should yield a negative value of skewness and a value less than one for balance, whereas a fatty ROI should yield a positive value of skewness and a value greater than one for balance. The skewness measure has been studied by Byng et al. (Ref. 66) to evaluate percent mammographic density in the breast. The two measures of balance using different percentages of the gray-level histogram are used to also quantify the skewness of the histogram.

Balance 1 (SeeRef. 97) is calculated as:

Balance 1=(95%CDF−AVG)/(AVG−5%CDF).

Balance 2 is calculated as:

Balance 2=(70%CDF−AVG)/(AVG−30%CDF).

Skewness is calculated as:

$$\text{Skewness} = \frac{m_3}{m_2^{3/2}}$$

wherein $$m_k = \sum_{i=0}^{G_h} n_i(i-\bar{i})^k / N$$

$$N = \sum_{i=0}^{G_h} n_i$$

$$\bar{i} = \sum_{i=0}^{G_h} n_i i$$

$n_i$ is the number of occurrences of gray-level value with index i, and $G_h$ is the highest gray-level value in the ROI.

Two features based on the spatial relationship among gray levels were investigated to characterize the texture patterns in the ROI. The coarseness and contrast measures first proposed by Amadasun et al. (Ref. 70) have been used to characterize Wolfe patterns by Tahoces et al. (Ref. 64). The mathematical definitions of the two texture features are given below. The amount of local variation in gray level corresponds visually with the level of coarseness (local uniformity) of a texture. As the amount of variation in gray level increases, the perceived uniformity (coarseness) of a texture decreases. Thus, the coarseness of a texture is obtained by quantifying the local variation in gray level. Since both the dynamic range of gray levels in an image and the spatial frequency of changes in gray level (amount of local gray-level variation) affect the contrast of a texture, the contrast measure includes two terms: the first term quantifies the differences among all gray levels in the ROI, and the second term quantifies the amount of local variation in gray level presented in the ROI. Note that the gray-level differences in an ROI are weighted by the amount of local variation. Thus, ROIs that have similar gray level differences may have different contrast depending on the local variation in the ROIs. Conversely, ROIs that have the same amount of local variation may have different contrast, depending on the gray level differences in the ROIs.

Coarseness or local uniformity is calculated as:

$$COS = \left[\sum_{i}^{G_h} p_i s(i)\right]^{-1}$$

Local Contrast is calculated as:

$$CON = \left[\frac{1}{N_g(N_g-1)}\sum_{i=0}^{G_h}\sum_{j=0}^{G_h} p_i p_j(i-j)^2\right]\left[\frac{1}{n^2}\sum_{i=0}^{G_h} s(i)\right]$$

wherein:
$N_g$ is the total number of different gray levels present in the ROI,
$G_h$ is the highest gray-level value in the ROI,
$p_i$ is the probability of occurrence of the gray-level value with index i,
N is the width of the ROI,
d is the neighborhood size (half of the operating kernel size),
n=N−2d, and
the ith entry of s is given by $$S(i) = \begin{cases} \sum |i - A_i| & \text{for } i \in \{N_i\} \text{ if } N_i \neq 0 \\ 0 & \text{otherwise} \end{cases}$$

in which $\{N_i\}$ is the set of pixels having gray level with index i $$A_i = \frac{1}{W-1}\sum_{p=-d}^{d}\sum_{p=-d}^{d} f(x+p, y+q) \ (p, q) \neq (0, 0)$$

to exclude $(x, y)$ $$W = (2d+1)^2 \quad (d=2)$$

The texture properties in each ROI are also analyzed using the two-dimensional Fourier transform. Background-trend correction is performed within the ROI prior to the application of the Fourier transform in order to eliminate the contribution of the variation from the gross anatomy of the breast background (low frequency component). The root-mean-square (RMS) variation and first moment of power (FMP) spectrum from the Fourier transform as defined below (Ref. 71) are calculated to quantify the magnitude and spatial frequency content of the fine underlying texture in the ROI after the background trend correction. The RMS variation and the first moment of the power spectrum have previously been investigated by Katsuragawa et al. (Ref. 72) to analyze interstitial disease in chest radiographs, by Tahoces et al. (Ref. 64) to classify Wolfe patterns in mammograms, and by Caligiuri et al. (Ref. 73) to characterize bone textures in skeletal radiographs.

RMS variation (root mean square of power spectrum) is calculated as:

$$RMS = \sqrt{\int\int |F(u,v)|^2 du dv}$$

FMP (first moment of power spectrum) is calculated as:

$$FMP = \int\int \sqrt{u^2+v^2}|F(u,v)|^2 du dv / \int\int |F(u,v)|^2 du dv$$

where $F(u,v) = \int\int f(x,y) e^{-j2\pi(xu+yv)} dx dy$. That is, $F(u,v)$ is the Fourier transform of the background corrected ROI.

Methods for Risk-modulated Diagnosis

Figure 8A:
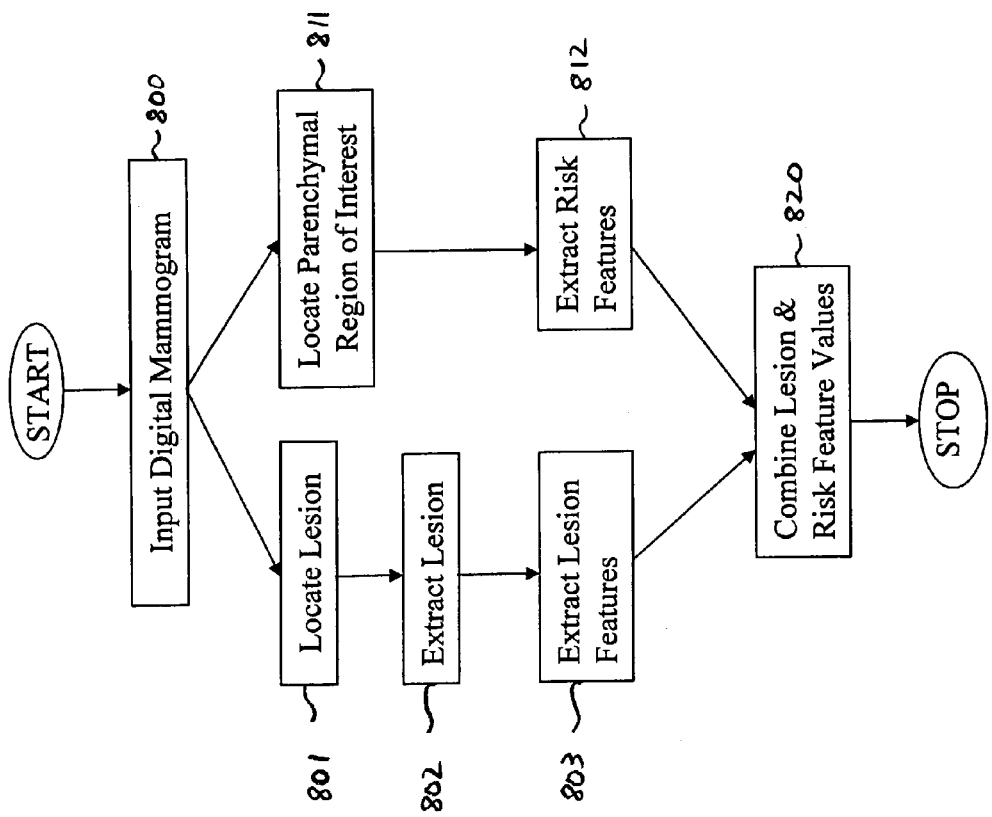
FIGS. 8A, 8B, and 8C show three exemplary methods and systems that characterize lesions on medical images using computerized analysis of the lesions, computerized assessment of risk based on computerized characterization of the local parenchymal pattern, and determination of a risk-modulated output regarding the lesion and disease of the patient.

FIGS. 8A–8A show three methods for risk-modulated diagnosis according to the present invention. The methods were tested using thirty malignant lesions and thirty benign lesions from mammographic cases in which both the left and right views were available.

FIG. 8A illustrates a method for incorporating lesion features with risk features in order to improve detection, diagnosis, and characterization. In step 800, a digital mammogram is obtained. Next, in steps 801–803, feature values associated with a lesion are extracted. In addition, in steps 811 and 812, risk feature values are extracted from a region of interest in the parenchymal region of the breast.

In step 801, a lesion is located within the digital mammogram obtained in step 800. In step 802, the pixels associated with the lesion within the digital mammogram are extracted and identified. In step 803, at least one of the lesion feature values described above is calculated.

In step 811, a region of interest with the parenchymal region of the digital mammogram is identified. Next, in step 812, at least one of the risk features described above is calculated using the pixel values comprising the region of interest selected in step 811.

In step 820, the lesion feature values and the risk feature values calculated in steps 803 and 812, respectively, are combined to determine a quantitative indication of whether the lesion is benign or malignant. For example, linear discriminant analysis (LDA) is used to merge the computer-extracted lesion features and the computer-extracted parenchymal risk features, which were extracted automatically from the image data by the computer system. An artificial neural network or other appropriate classifier may be used in step 820. The computer-extracted lesion features included radial gradient (RGI), FWHM, texture, gray level, and margin sharpness. The computer-extracted parenchymal features (risk features) include skewness, balance 1, balance 2, contrast, and coarseness, all of which were extracted in the contralateral mammogram. If the lesion was in the right breast, the texture analysis on the "normal" parenchyma was performed on the left breast. The merged features were trained and evaluated in the task of distinguishing between malignant and benign lesions with ROC (receiver operating characteristic) analysis, with the area under the ROC curve (Az) used as the performance index. In one study, the computer-extracted lesion features yielded an Az of 0.85 and the merged risk features yielded an Az of 0.81. By combining both the lesion and risk features, the classifier yielded an Az of 0.92.

Figure 8B:
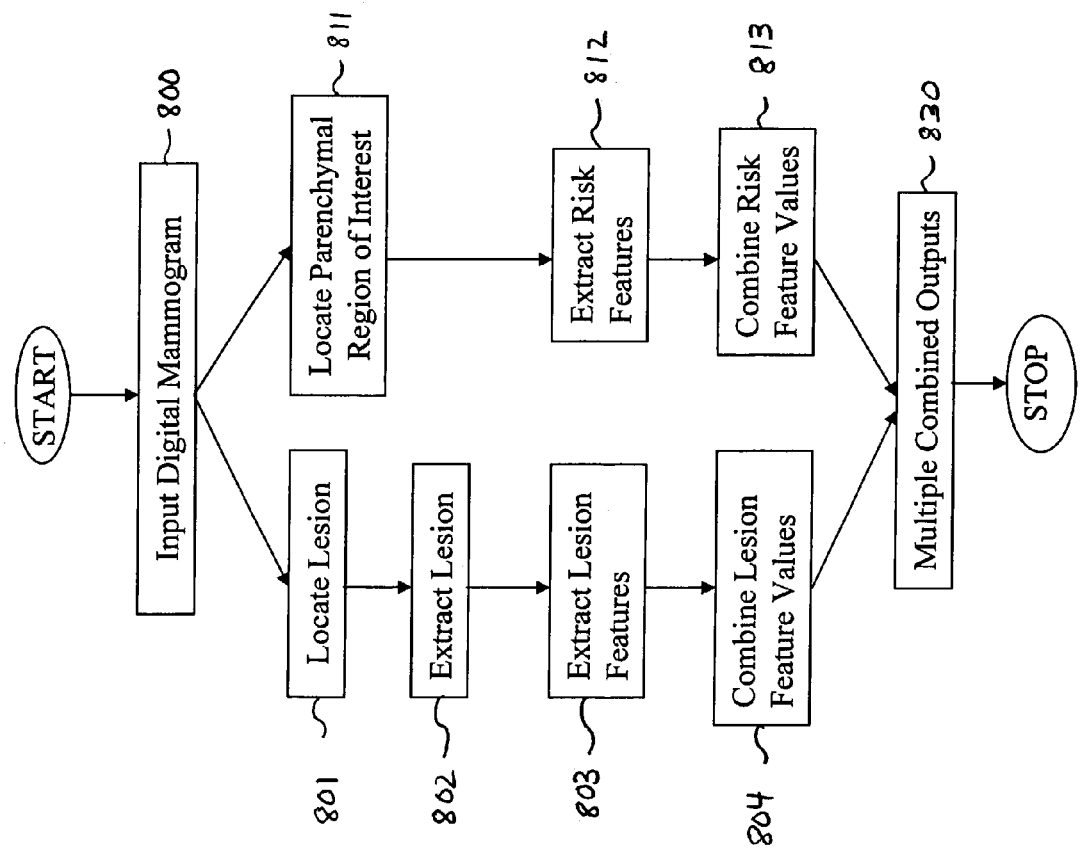

FIG. 8B illustrates a second embodiment of a method for risk-modulated diagnosis according to the present invention. Note that in FIG. 8B, steps 800, 801, 802, 803, 811, and 812 are identical to the similarly identified steps shown in FIG. 8A.

In step 804, the lesion feature values calculated in step 803 are combined, e.g., using linear discriminant analysis to determine an indication of whether the lesion is benign or malignant. Similarly, in step 813, the risk features values calculated in step 813 are combined to determine whether the individual associated with the digital mammogram is a high or low risk individual. Note that an artificial neural network or other appropriate classifier may be used in step 804 and/or step 813.

In step 830, the output from each LDA (calculated in steps 804 and 813) is normalized and then multiplied together in step 830 to yield a risk-modulated measure characterizing the lesion. The classifier output that characterizes the lesion is weighted by the output from the risk classifier. As discussed above, the individual LDAs yielded Az values of 0.85 and 0.81 for the lesion and risk estimations, respectively. Using the multiplication of the normalized outputs, the combined classifier gives an Az value of 0.93. Note that in this example, the lesion classifier was trained in the task of distinguishing between malignant and benign lesions, and the risk classifier was trained in the task of distinguishing between high and low risk individuals. The combined classifier using the multiplicative method was tested in terms of its ability to distinguish between malignant and benign lesions.

Figure 8C:
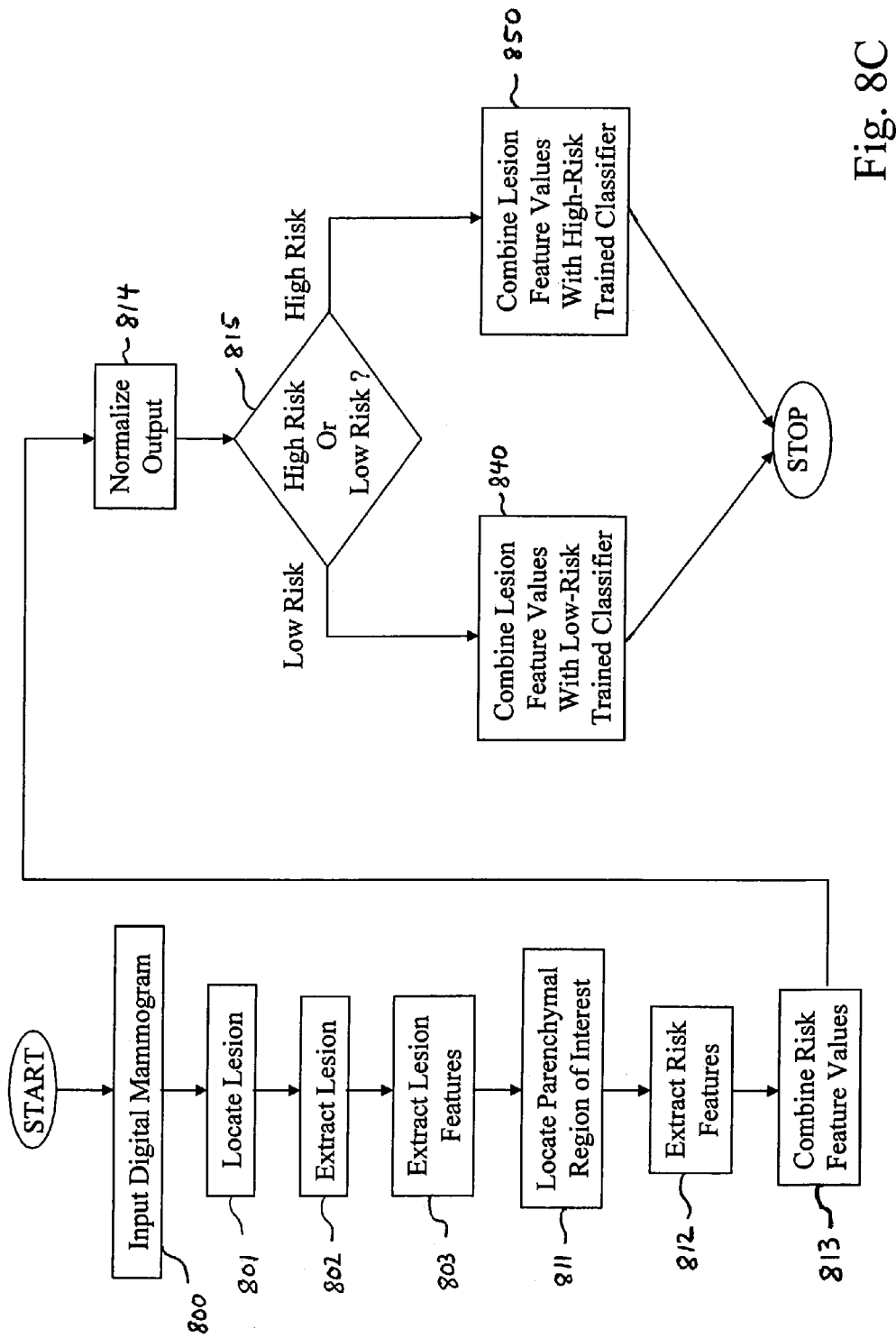

FIG. 8C illustrates a third embodiment of a method for risk-modulated diagnosis according to the present invention. Steps 800–803 and 811–813 are the same as described above with reference to FIGS. 8A and 8B. Here the risk classifier (using, e.g., a LDA) is trained with, e.g., four risk parenchymal features, in the task of distinguishing between high- and low-risk individuals.

In step 814, the output of step 813 is normalized. In step 815, a threshold is then used on the normalized LDA (or classifier) output to separate the individual into the high risk population or the low risk population. For example, based on previous data, one can use the computer-extracted risk features that correspond to a Gail model risk output of less than 20% for the low risk group. Anything higher than 20% can be considered as high risk.

The lesion classifier is retrained with the (in this case) five lesion features separately, for the high risk group and the low risk group. If the inquiry in step 815 determines that the individual is low risk, the lesion feature values are combined with a low-risk classifier in step 840 to determine whether the lesion is benign or malignant. Likewise, if the inquiry in step 815 determines that the individual is high risk, the lesion feature values are combined using a high-risk classifier in step 850 to determine whether the lesion is benign or malignant. Note that an artificial neural network or other appropriate classifier may be used in step 840 and/or step 850.

In a study of the above methods, the results yielded an Az of 0.85 when all cases are used with the lesion classifier (as given in FIG. 8A), an Az of 0.965 for the high-risk group, and an Az of 0.77 for the low-risk group. The threshold used in this example for separating between high risk cases and low risk cases using the output from the risk classifier was 0.40 after normalization.

It is evident from these three embodiments that the incorporation of risk information, obtained from the computerized analysis of "normal" parenchyma, can help in the diagnosis of suspect lesions. Likewise, weighing computerized detection results by computer-extracted features that characterize the local surrounding parenchyma can be expected to improve diagnoses in a similar fashion. In addition, knowledge of the characteristics of the lesion and its parenchymal surrounding tissue can yield information on the lesion as well as its environment.

Although the risk-modulated CAD method of the present invention has been presented in the context of processing mammographic breast images, the method can be implemented using other breast images, e.g., sonographic breast images, in which a computerized image analysis is performed with respect to cancer or some other disease state. For example, using sonographic breast images, ultrasound lesions characteristics such as lesion margin sharpness and posterior acoustic characteristics can be used as lesion feature values in the method of the present invention. Moreover, the calculation of ultrasonic lesion characteristics is known in this art. See U.S. Pat. No. 5,984,870 (Giger et al., Method and system for the automated analysis of lesions in ultrasound images), the contents of which are incorporated herein by reference. In addition, texture analysis on the sonographic parenchyma can be used as a risk feature value in a manner analogous to the use of the risk feature values described above for digital mammographic images. See U.S. Pat. No. 6,282,305 (Huo et al., Method and system for the computerized assessment of breast cancer risk), the contents of which are incorporated herein by reference.

The present method can also be implemented more generally on other medical images of other organs (e.g., chest radiographs, or CT scans of the thorax, abdomen, or skeletal system) with respect to some other disease state or state of risk. Lesion and risk feature values can readily be obtained from other medical images by those of ordinary skill in the art. For example, characteristics associated with a detected benign colonic polyp can be used as risk feature values to modulate quantitative measures of malignancy calculated in methods of detecting cancerous polyps using colonographic images. The detection of such colonic polyps is discussed in U.S. patent application Ser. No. 10/270,674 (Yoshida et al., Method for the computer-aided detection of three-dimensional lesions), the contents of which are incorporated herein by reference. Moreover, the detection of lesion feature values in various medical images is also well known in this art. See, e.g., U.S. Pat. No. 5,881,124 (Giger et al., Automated method and system for the detection of lesions in medical computed tomographic scans), the contents of which are incorporated herein by reference.

For the purposes of this description, an image is defined to be a representation of a physical scene, in which the image has been generated by some imaging technology: examples of imaging technology could include television or CCD cameras or X-ray, sonar, or ultrasound imaging devices. The initial medium on which an image is recorded could be an electronic solid-state device, a photographic film, or some other device such as a photostimulable phosphor. That recorded image could then be converted into digital form by a combination of electronic (as in the case of a CCD signal) or mechanical/optical means (as in the case of digitizing a photographic film or digitizing the data from a photostimulable phosphor). The number of dimensions that an image could have could be one (e.g. acoustic signals), two (e.g. X-ray radiological images), or more (e.g. nuclear magnetic resonance images).

As disclosed in cross-referenced patent application Ser. No. 09/773,636, FIG. 9 of that patent application is a schematic illustration of a general purpose computer 900 which can be programmed according to the teachings of the present invention. In FIG. 9 of the cross-referenced U.S. patent application Ser. No. 09/773,636, the computer 900 can be used to implement the processes of the present invention, wherein the computer includes, for example, a display device 902 (e.g., a touch screen monitor with a touch-screen interface, etc.), a keyboard 904, a pointing device 906, a mouse pad or digitizing pad 908, a hard disk 910, or other fixed, high density media drives, connected using an appropriate device bus (e.g., a SCSI bus, an Enhanced IDE bus, an Ultra DMA bus, a PCI bus, etc.), a floppy drive 912, a tape or CD ROM drive 914 with tape or CD media 916, or other removable media devices, such as magneto-optical media, etc., and a mother board 918. The mother board 918 includes, for example, a processor 920, a RAM 922, and a ROM 924 (e.g., DRAM, ROM, EPROM, EEPROM, SRAM, SDRAM, and Flash RAM, etc.), I/O ports 926 which may be used to couple to an image acquisition device and optional special purpose logic devices (e.g., ASICs, etc.) or configurable logic devices (e.g., GAL and re-programmable FPGA) 928 for performing specialized hardware/software functions, such as sound processing, image processing, signal processing, neural network processing, automated classification, etc., a microphone 930, and a speaker or speakers 932.

As stated above, the system of the present invention includes at least one computer readable medium. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Such computer readable media further includes the computer program product of the present invention for performing any of the processes according to the present invention, described above. The computer code devices of the present invention can be any interpreted or executable code mechanism, including but not limited to scripts, interpreters, dynamic link libraries, Java classes, and complete executable programs, etc.

The programming of general purpose computer 900 (disclosed in cross-referenced patent application Ser. No. 09/773,636) may include a software module for digitizing and storing images obtained from film or an image acquisition device. Alternatively, the present invention can also be implemented to process digital data derived from images obtained by other means, such as a picture archive communication system (PACS). In other words, the digital images being processed may be in existence in digital form and need not be converted to digital form in practicing the invention.

Accordingly, the mechanisms and processes set forth in the present description may be implemented using a conventional general purpose microprocessor or computer programmed according to the teachings in the present specification, as will be appreciated by those skilled in the relevant art(s). Appropriate software coding can readily be prepared by skilled programmers based on the teachings of the present disclosure, as will also be apparent to those skilled in the relevant art(s). However, as will be readily apparent to those skilled in the art, the present invention also may be implemented by the preparation of application-specific integrated circuits or by interconnecting an appropriate network of conventional component circuits.

The present invention thus also includes a computer-based product which may be hosted on a storage medium and include instructions which can be used to program a general purpose microprocessor or computer to perform processes in accordance with the present invention. This storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Numerous modifications and variations of the present invention are possible in light of the above teachings. It is therefore to be understood that within the scope of the appended claims and their equivalents, the invention may be practiced otherwise than as specifically described herein.

The invention claimed is:

1. A method of calculating a disease assessment by analyzing a medical image, comprising:
   extracting at least one lesion feature value from the medical image;
   extracting at least one risk feature value from the medical image; and
   determining the disease assessment based on the at least one lesion feature value and the at least one risk feature value.

2. The method of claim 1, wherein the step of extracting the at least one lesion feature value comprises:
   locating a lesion in the medical image;
   segmenting lesion image data corresponding to the located lesion; and
   extracting the at least one lesion feature value from the segmented lesion image data.

3. The method of claim 2, wherein the step of extracting the at least one lesion feature value comprises:
   extracting at least one feature value selected from the group consisting of margin sharpness, degree of spiculation, density, homogeneity, texture, asymmetry, shape, and temporal stability of the lesion.

4. The method of claim 2, wherein the determining step comprises:
   determining, based on the at least one lesion feature value and the at least one risk feature value, at least one of (1) a likelihood that the lesion is malignant, (3) a stage of disease of the lesion, and (4) a likelihood that a future malignancy will develop, as the disease assessment.

5. The method of claim 1, wherein the step of extracting at least one risk feature value comprises:
   locating a region of interest (ROI) in the medical image corresponding to a parenchymal region; and
   extracting the at least one risk feature value from the ROI.

6. The method of claim 5, wherein the step of extracting the at least one risk feature value comprises:
   extracting at least one feature value indicating a maximum gray level of the ROI, a minimum gray level of the ROI, an average gray level of the ROI, a skewness of the ROI, a coarseness of the ROI, a contrast of the ROI, a root mean square variation of a power spectrum of the ROI, and a first moment of the power spectrum of the ROI.

7. The method of claim 1, wherein the determining step comprises:
   calculating a quantitative measure of malignancy as the disease assessment by applying the at least one lesion feature value and the at least one risk feature value to a classifier.

8. The method of claim 7, wherein the calculating step comprises:
   calculating the quantitative measure of malignancy as the disease assessment by applying the at least one lesion feature value and the at least one risk feature value to a linear discriminant.

9. The method of claim 7, wherein the calculating step comprises:
   calculating the quantitative measure of malignancy as the disease assessment by applying the at least one lesion feature value and the at least one risk feature value to an artificial neural network.

10. The method of claim 7, wherein the calculating step comprises:
    training the classifier in relation to the at least one lesion feature value and the at least one risk feature value obtained from a set of previously obtained medical images based on a measure of malignancy associated with the previously obtained medical images.

11. The method of claim 1, wherein the determining step comprises:
    calculating a quantitative measure of risk by applying the at least one risk feature value to a first classifier;
    calculating a quantitative measure of malignancy by applying the at least one lesion feature value to a second classifier; and
    weighting the quantitative measure of malignancy by the quantitative measure of risk to obtain the disease assessment.

12. The method of claim 11, wherein:
    the step of calculating the quantitative measure of risk comprises calculating the quantitative measure of risk by applying the at least one risk feature value to a first linear discriminant; and
    the step of calculating the quantitative measure of malignancy comprises calculating the quantitative measure of malignancy by applying the at least one lesion feature value to a second linear discriminant.

13. The method of claim 11, wherein:
    the step of calculating the quantitative measure of risk comprises calculating the quantitative measure of risk by applying the at least one risk feature value to a first artificial neural network; and
    the step of calculating the quantitative measure of malignancy comprises calculating the quantitative measure of malignancy by applying the at least one lesion feature value to a second artificial neural network.

14. The method of claim 11, wherein the step of calculating the quantitative measure of risk comprises:
    training the first classifier in relation to the at least one risk feature value obtained from a set of previously obtained medical images based on a measure of risk associated with the previously obtained medical images.

15. The method of claim 11, wherein the step of calculating the quantitative measure of malignancy comprises:
    training the second classifier in relation to the at least one lesion feature value obtained from a set of previously obtained medical images based on a measure of malignancy associated with the previously obtained medical images.

16. The method of claim 1, wherein the determining step comprises:
    determining a quantitative measure of risk by applying the at least one risk feature value to a first classifier;
    classifying the quantitative measure of risk as high risk if the quantitative measure of risk exceeds a predetermined threshold risk value;
    determining the disease assessment by applying the at least one lesion feature value to a second classifier, if the quantitative measure of risk is classified as high risk; and
    determining the disease assessment by applying the at least one lesion feature value to a third classifier, if the quantitative measure of risk is not classified as high risk.

17. The method of claim 16, wherein the step of calculating the quantitative measure of risk comprises:
    training the first classifier in relation to the at least one risk feature value obtained from a set of previously obtained medical images based on a measure of risk associated with the previously obtained medical images.

18. The method of claim 16, wherein the step of determining the disease assessment when the quantitative measure of risk is classified as high risk comprises:

training the second classifier in relation to the at least one lesion feature value obtained from a set of previously obtained high-risk medical images based on a measure of malignancy associated with the previously obtained high-risk medical images.

19. The method of claim 16, wherein the step of determining the disease assessment when the quantitative measure of risk is not classified as high risk comprises:

training the third classifier in relation to the at least one lesion feature value obtained from a set of previously obtained low-risk medical images based on a measure of malignancy associated with the previously obtained low-risk medical images.

20. The method of claim 1, wherein:

the step of extracting at least one lesion feature value from the medical image comprises extracting at least one lesion feature value from a lesion extracted from a digital mammogram; and the step of extracting at least one risk feature value from the medical image comprises extracting at least one risk feature value from a parenchymal region of the digital mammogram.

21. A system configured to calculate a disease assessment by analyzing a medical image by performing the steps recited in any one of claims 1–20.

22. A computer readable medium configured to store plural computer program instructions which, when executed by a computer, cause the computer perform the steps recited in any one of claims 1–20.

* * * * *